(12) United States Patent
Mahboubi

(10) Patent No.: US 8,871,226 B2
(45) Date of Patent: Oct. 28, 2014

(54) METHODS AND COMPOSITIONS FOR THE TREATMENT AND DIAGNOSIS OF CANCER

(75) Inventor: Zine El Abidine Mahboubi, Budapest (HU)

(73) Assignee: Hafid Mahboubi, Edinburgh (GB)

( * ) Notice: Subject to any disclaimer, the term of this patent is extended or adjusted under 35 U.S.C. 154(b) by 0 days.

(21) Appl. No.: 12/689,658

(22) Filed: Jan. 19, 2010

(65) Prior Publication Data
US 2010/0119555 A1 May 13, 2010

Related U.S. Application Data

(63) Continuation of application No. 10/544,748, filed as application No. PCT/GB2004/000471 on Feb. 6, 2004, now abandoned.

(30) Foreign Application Priority Data

Feb. 6, 2003 (GB) ................................. 0302691.1

(51) Int. Cl.
| | | |
|---|---|---|
| *A61K 39/00* | (2006.01) | |
| *C12Q 1/04* | (2006.01) | |
| *G01N 33/574* | (2006.01) | |
| *A61K 31/00* | (2006.01) | |
| *A61K 31/7048* | (2006.01) | |
| *A61K 31/4196* | (2006.01) | |
| *A61K 31/496* | (2006.01) | |
| *G01N 33/569* | (2006.01) | |
| *G01N 33/68* | (2006.01) | |

(52) U.S. Cl.
CPC .......... *A61K 31/7048* (2013.01); *G01N 33/574* (2013.01); *A61K 31/00* (2013.01); *G01N 2333/40* (2013.01); *A61K 31/4196* (2013.01); *G01N 2800/2828* (2013.01); *A61K 39/0011* (2013.01); *A61K 39/0002* (2013.01); *A61K 31/496* (2013.01); *G01N 33/56961* (2013.01); *A61K 39/0007* (2013.01); *G01N 33/6896* (2013.01)
USPC .......................................... 424/274.1; 435/5

(58) Field of Classification Search
CPC .................................. A61K 39/00; C12N 15/62
See application file for complete search history.

(56) References Cited

U.S. PATENT DOCUMENTS

| 5,707,816 | A | 1/1998 | Vojdani | |
|---|---|---|---|---|
| 5,908,855 | A * | 6/1999 | Camden | ........................ 514/383 |
| 6,488,929 | B2 | 12/2002 | Cutler et al. | |
| 6,875,422 | B2 * | 4/2005 | Nonomura et al. | ............. 424/49 |

OTHER PUBLICATIONS

McCullough et al. Oral Oncology, 2002, vol. 38, p. 391-393 in IDS of Feb. 21, 2007 of the parent U.S. Appl. No. 10/544,748.*
Scully Oral Biology and Medicine, 1994, vol. 5, p. 125-157 on Apr. 16, 2008 in parent U.S. Appl. No. 10/544,748.*
Como and Dismukes, 1994, The New England Journal of Medicine. p. 263-272.*
Tapazoglou et al. (American Journal of Clinical Oncology, 1986, vol. 5, p. 369-375.*
Viscoli et al. (European Journal of Cancer, 1996, vol. 32A, p. 814-820).*
Mattiuzzi et al. (Cancer Jan. 2003, vol. 97, p. 450-456).*
Naijd et al. (Tumori, 1991, vol. 77, p. 385-390).*
Como and Dismukes (Drug Therapy, 1994, The New England Journal of Medicine, p. 263-272 of record on Oct. 11, 2012).*
Gottfredsson et al. Cancer, published in May 2003, vol. 98, p. 24-30.*
Gottfredsson et al. Cancer, published in May 2003, vol. 98, p. 24-30 of record on Sep. 16, 2013.*
Barrett et al. Oral Diseases, 1998, vol. 4, p. 26-31.
R. Demaimay et al., "Late Treatment With Polyene Antibiotics Can Prolong the Survival Time of Scrapie-Infected Animals", *Journal of Virology, The American Society for Microbiology*,US, 71(12): 9685-9689 (1997).
D. McKenzie et al., "Amphotericin B Delays Both Scrapie Agent Replication and PRP-RES Accumulation Early in Infection",*Journal of Virology, The American Society for Microbiology*, US, 68(11): 7534-7536 (1994).
M. McCullough et al., "Oral Yeast Carriage Correlates With Presence of Oral Epithelial Dysplasia", *Oral Oncolo, Elsevier Science*, GB, 38(4): 391-393 (2002).
W. G. Crook & J. Tenn., "Depression Associated With Candida Albicans Infections", *JAMA*, 251(22): 2928-2929 (1984).
F. Pallavicini et al., "Evaluation of the Utility of Serological Tests in the Diagnosis of Candidemia", *Minerva Anestesiologica*, 65(9): 637-639 (1999).
Sully Oral Biology and Medicine, 1994, vol. 5, p. 125-157.

* cited by examiner

*Primary Examiner* — Agnieszka Boesen
(74) *Attorney, Agent, or Firm* — Drinker Biddle & Reath LLP

(57) ABSTRACT

The invention provides methods of treatment of prion disease, cancers and other conditions, the methods comprising administration of an anti-*Candida* agent. Also disclosed are methods of diagnosing prion disease and cancers, said methods based on the determination of the presence of *Candida* infection, in particular systemic candidiasis.

7 Claims, 36 Drawing Sheets

Figure 26 - Goose Oesophagus

Figure 27 - Goose Ovary 2
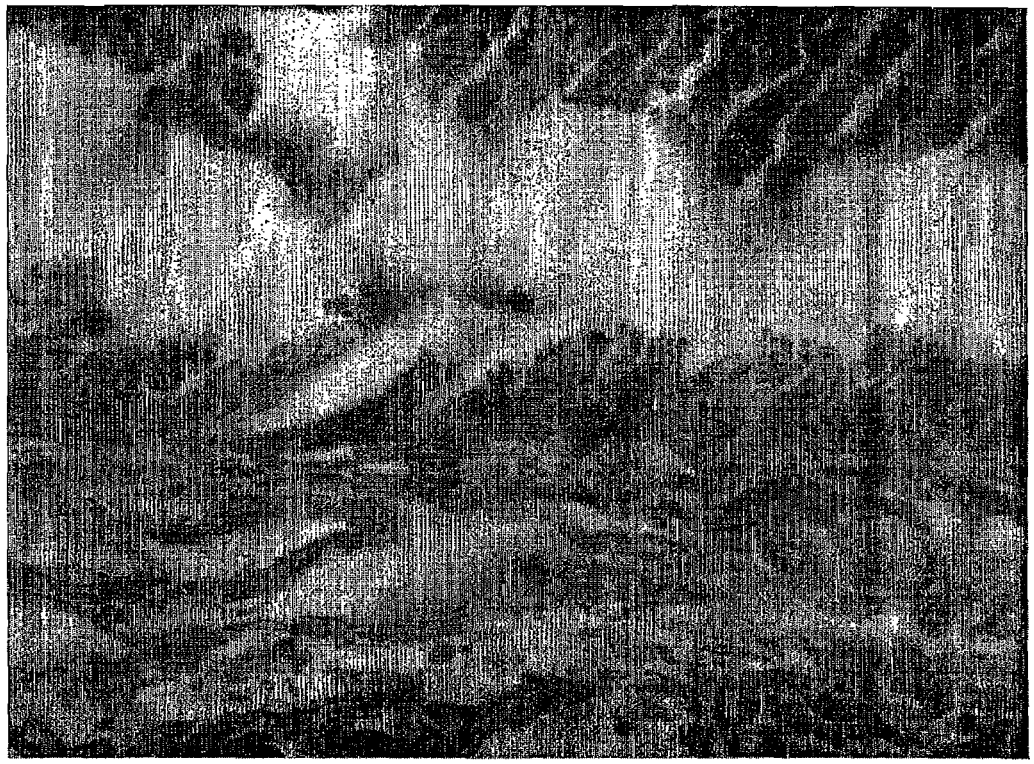

Figure 28 - Goose Ovary
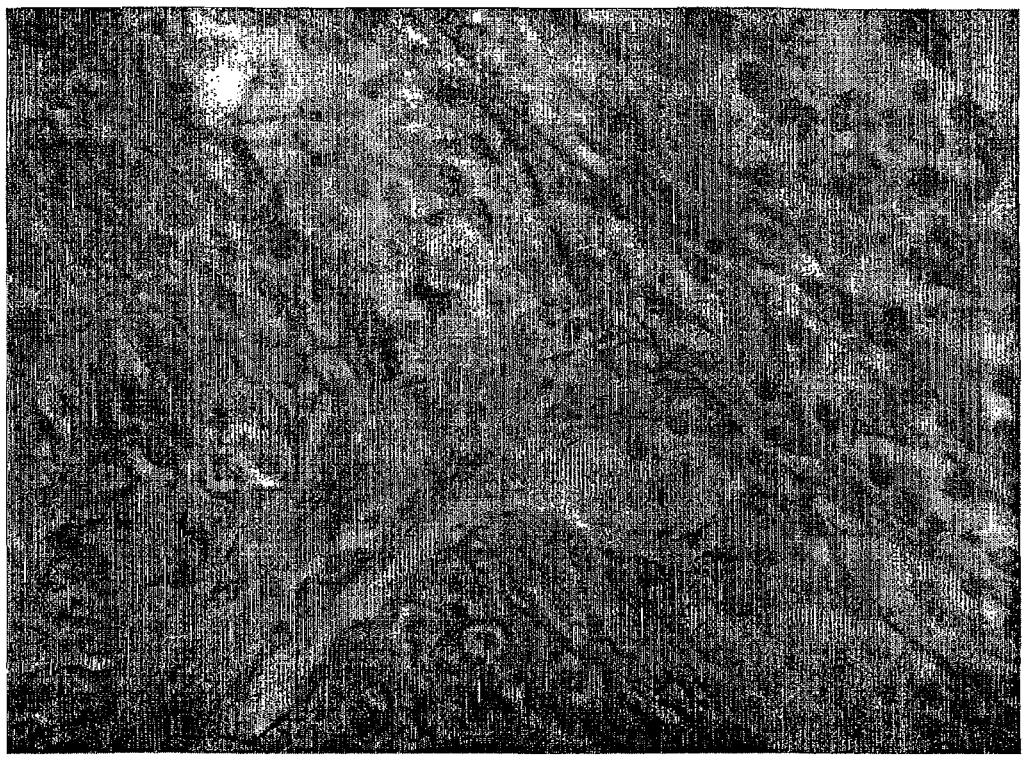

Figure 29 - Rabbit Lung
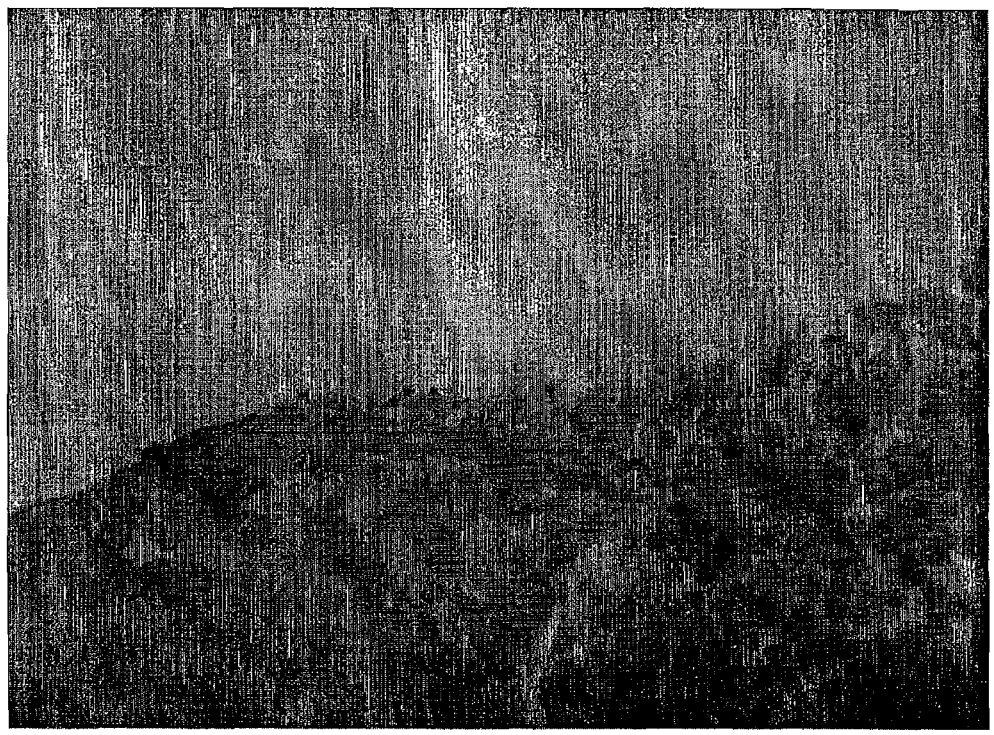

Figure 30 - Rabbit Oesophagus
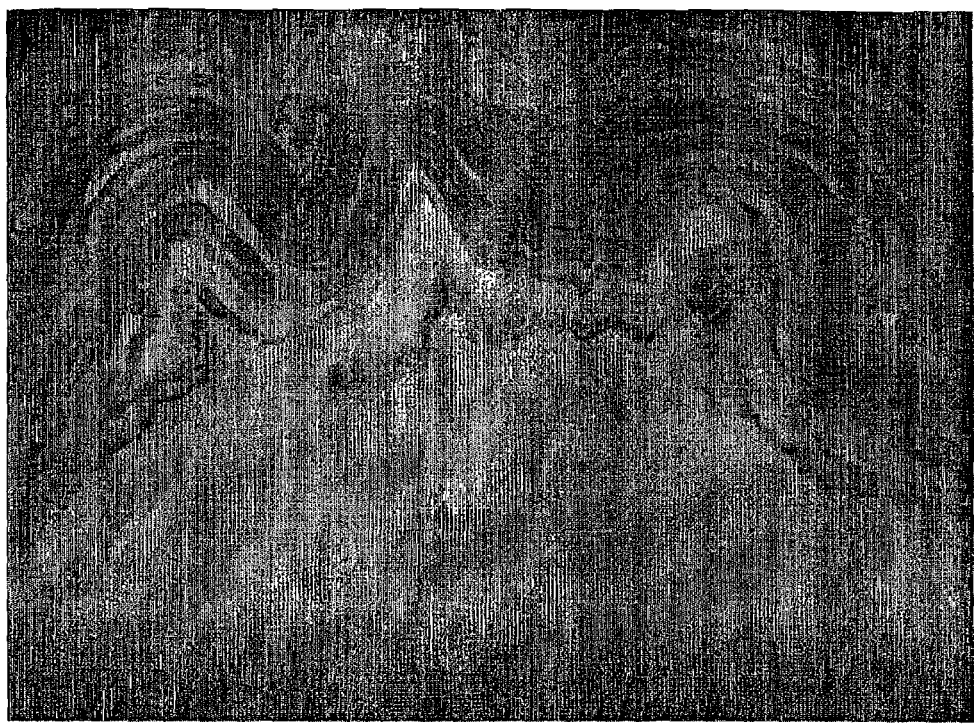

Figure 31 - Rabbit Ovary 2

Figure 32 - Rabbit Ovary
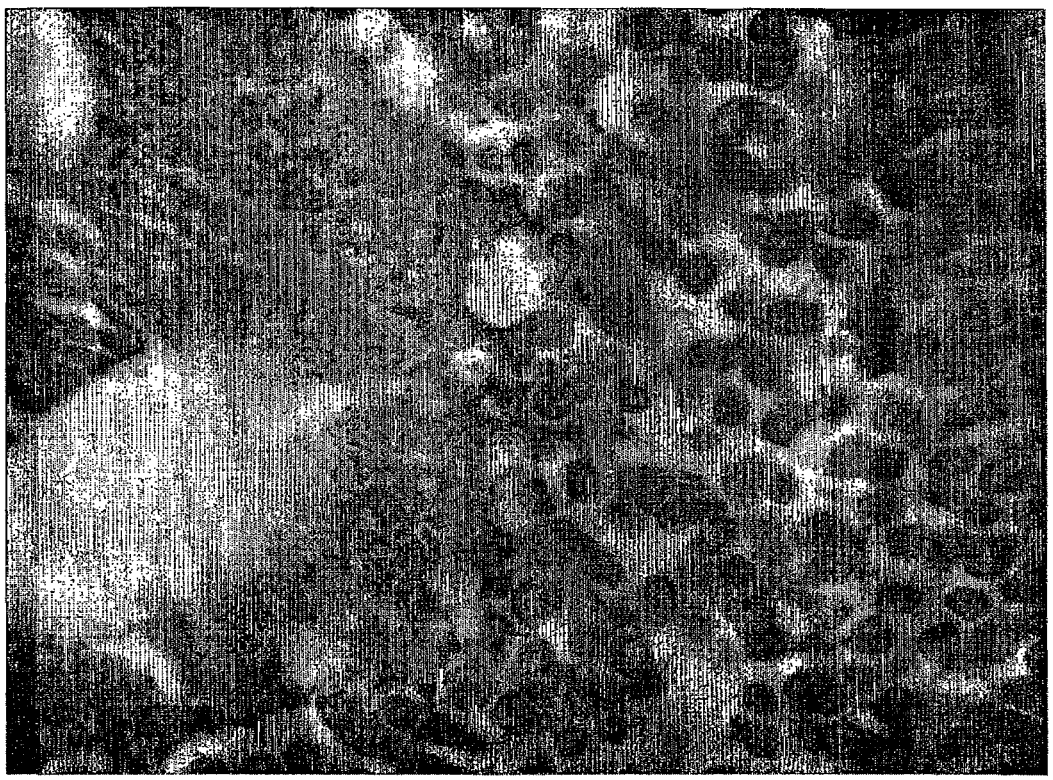

Figure 33 - Rabbit Tongue
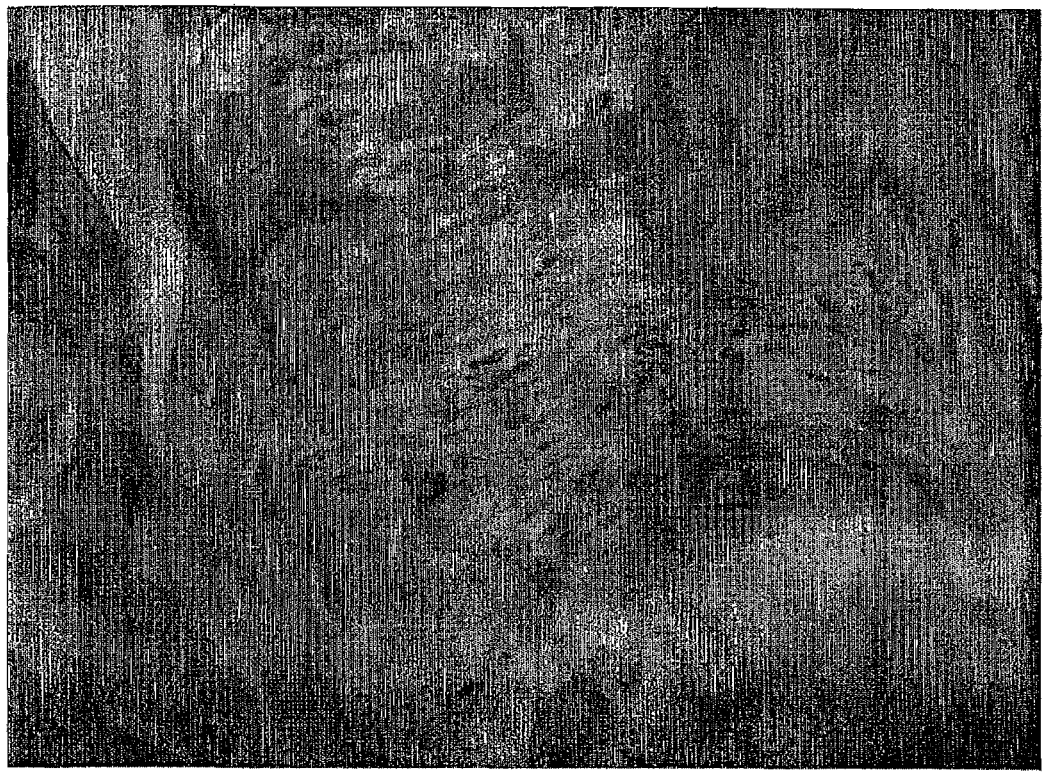

Figure 34 - Swine Brain
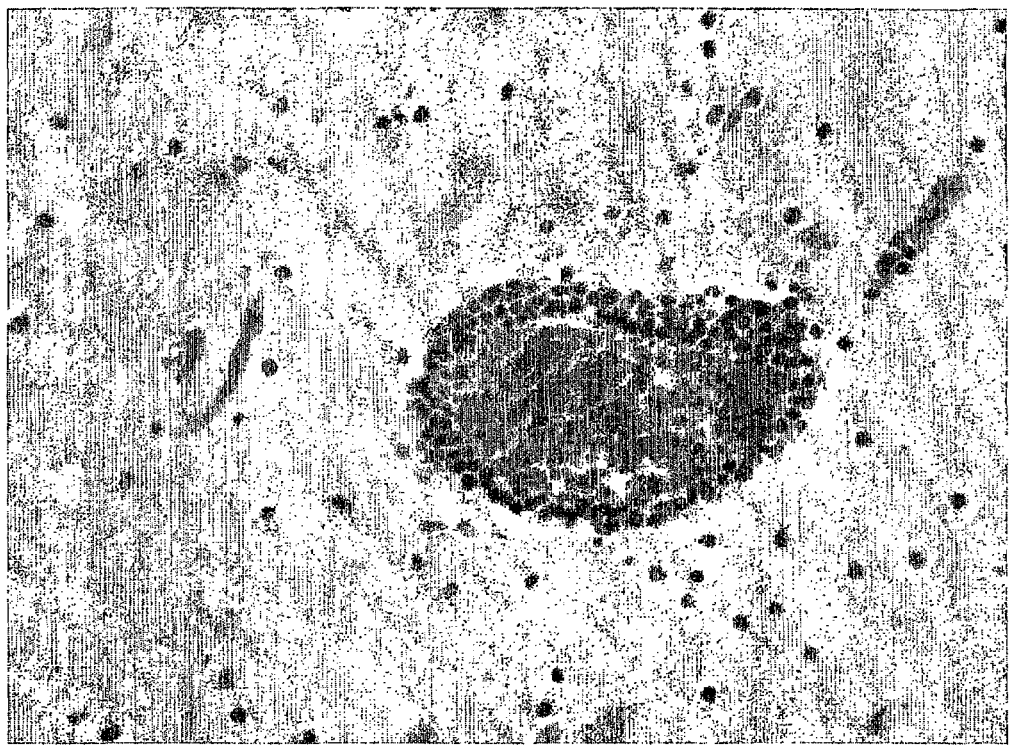

Figure 35 - Swine Kidney
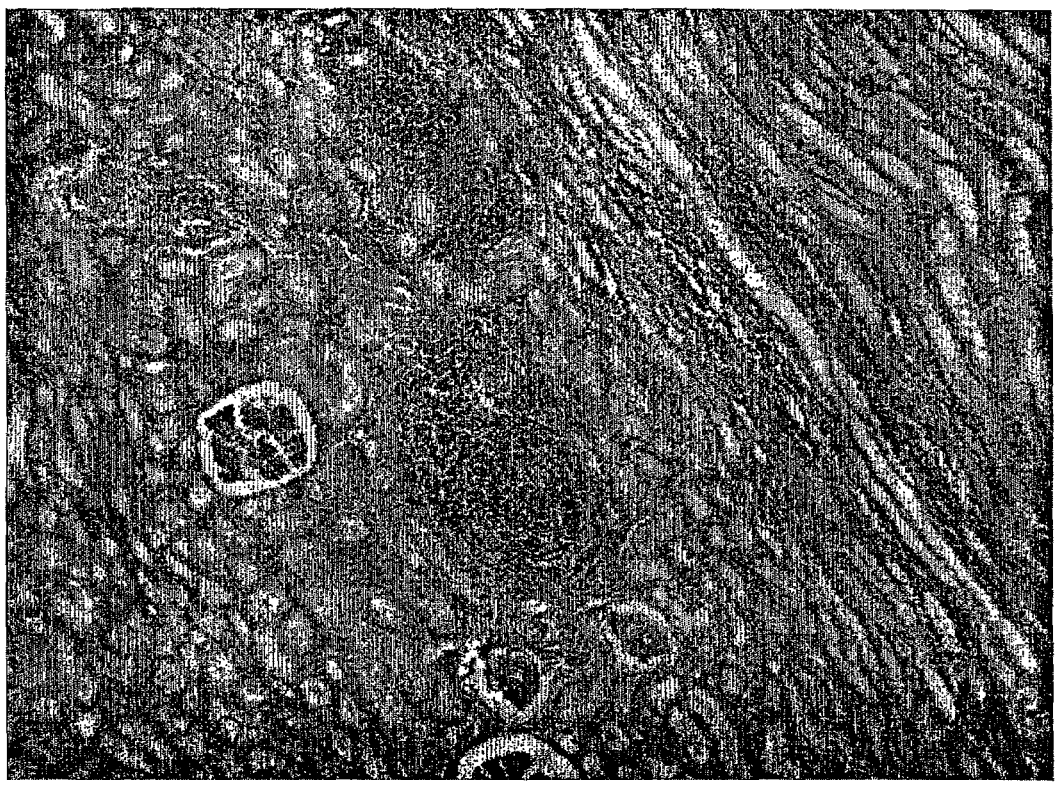

Figure 36 - Swine Ovary
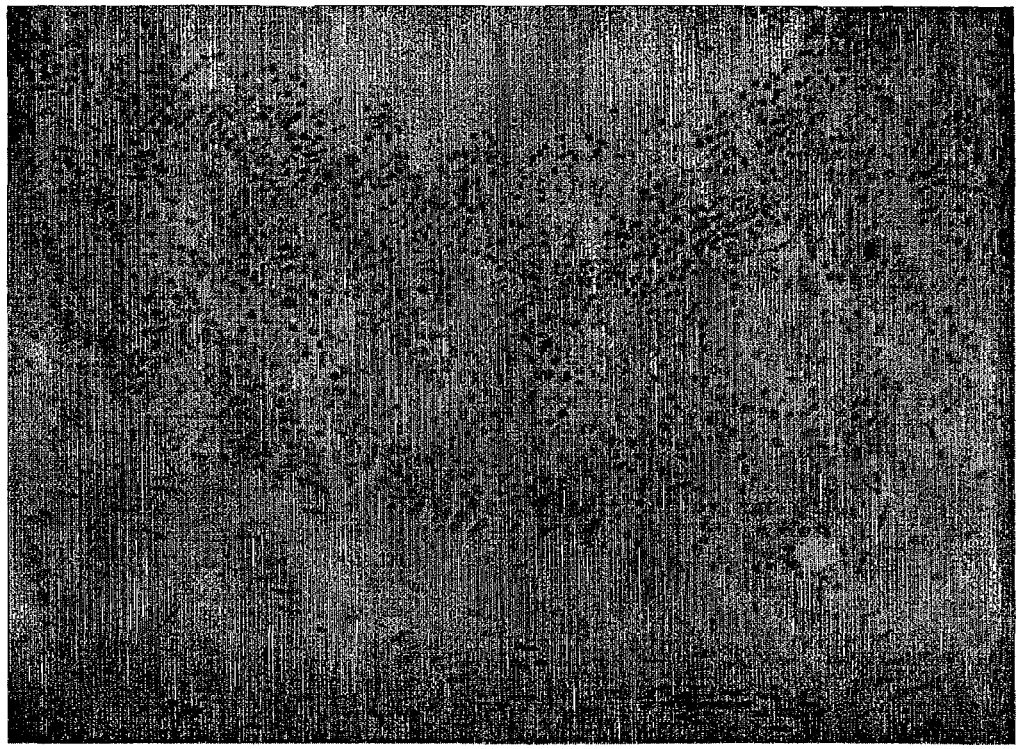

METHODS AND COMPOSITIONS FOR THE TREATMENT AND DIAGNOSIS OF CANCER

CROSS-REFERENCE TO RELATED APPLICATION

This application is a continuation of copending U.S. application Ser. No. 10/544,748, filed May 30, 2006, which is the U.S. national phase of PCT/GB2004/000471, filed Feb. 6, 2004, the entire disclosure of which is incorporated herein by reference.

The present invention relates to methods of treatment and diagnosis and compositions for use in such therapy. In particular, the present invention relates to methods of diagnosing and treatment of prion related conditions and methods of diagnosing and treatment of cancer.

Prion diseases are believed to occur in most mammals. They include diseases such as scrapie in sheep, bovine spongiform encephalopathy (BSE) in cattle, transmissible mink encephalopathy (TME) in mink and chronic wasting disease (CWD) in deer and elk. Prion disease of humans include sporadic and familial Creutzfeldt-Jakob disease (CJD), kuru, Fatal Familial Insomnia (FFI), Gerstmann Straussler Scheinker syndrome (GSS) and Alpers syndrome.

Prion diseases are characterized by the formation and accumulation in the brain of an abnormal isoform (PrPsc) of a normal protein (PrPc), which is host-encoded by a single exon of a single copy gene. PrPc is found on both neural and non-neural tissues, with expression predominant on the surface of neurones. PrPc is predominantly alpha-helical, contains almost no beta sheet structure, and is protease-sensitive. In contrast, the modified form (PrPsc) accumulates in the cytoplasmic vesicles of diseased individuals, has a higher beta sheet content, and is proteinase K resistant.

It has been proposed that the safe form of the protein, PrPc, is normally adopted but rarely switches to the infective prion (PrPsc). Mutations are believed to favour the switch to PrPsc with PrPsc believed to be transdominant, causing switching from PrPc to molecular aggregates of PrPsc in an exponential fashion.

The formation of such aggregates of PrPsc is closely associated with brain pathology in which amyloid deposits of PrPsc are formed in the brain, which eventually becomes "spongiform" (filled with holes). Symptoms associated with prion diseases are loss of motor control, dementia, paralysis, wasting and eventually death. Post-mortem analysis typically shows the presence of non-inflammatory lesions, vacuoles, amyloid protein deposits and astrogliosis. Indeed, the characteristic post-mortem appearance of prion disease infected brain tissue with large vacuoles in the cortex and cerebellum has led to prion diseases being otherwise known as transmissible spongiform encephalopathies (TSEs). Until recently, the incidence and risk of TSE diseases in humans was considered to be relatively rare, being believed to be limited to, for example, isolated tribes of the Fore people of New Guinea, in which ritualistic cannibalism was practiced. However, following the bovine spongiform encephalopathy (BSE) epidemic in the late 1980s and early 1990s, believed to be caused by the feeding of animal parts to cattle in feed, and experiments showing inter-species transmission of BSE, concerns were raised of the risk to humans. In 1996, a new variant of CJD was identified in the British population and has subsequently been attributed to ingestion of BSE infected beef. Iatrogenic CJD has also been attributed to administration of human growth hormone derived from cadaveric pituitaries, transplanted dura mater and corneal grafts.

Early stages of variant Creutzfeldt-Jakob disease are dominated by psychiatric symptoms, such as dysphoria, withdrawal, anxiety, and insomnia. A significant proportion of patients also exhibit neurological symptoms within four months of clinical onset, including poor memory, pain, sensory symptoms, and unsteadiness of gait.

The diagnosis of vCJD is dependent on clinical neurological assessment. Diagnosis typically involves magnetic resonance imaging to exclude other problems such as tumour. Moreover, a characteristic abnormality can be seen in 80 percent or more of cases which may be very useful in arriving at a diagnosis. Blood and other biochemical tests are usually normal. The presence of certain proteins within the cerebrospinal fluid (particularly a protein called 14-3-3) may be helpful. A brain biopsy (sampling of brain tissue) may be carried out to detect signs of spongiform change. Tonsil biopsy may also be useful. However, as with the other forms of CJD, at present a definite diagnosis is only possible by examining the brain during a post-mortem examination, in which the characteristic signs of spongiform change, loss of neurons and the presence of so-called florid plaques may be evident.

The mechanism for inter-species transmission of TSEs is not fully understood. However, recently, a study in yeast cells has indicated that prions may adopt a number of different conformations, allowing them to more easily invade a new host. Yeast cells manufacture a protein called Sup35, which displays prion-like behaviour, forming aggregates and converting its normal counterpart to the prion version. In Cell 2000, 100:277-288, Chien and Weissman reported the prion version of Sup35 in one yeast species was unable to convert Sup35 of a different yeast species into the prion version, and vice versa. However, in a later study, the same authors reported that a chimaeric prion, which combined Sup35 segments *Saccharomyces cerevisiae* and *Candida albicans* could adopt the shape of the prion specific for each species when introduced into each individual species (Nature 2001, 410: 223-227), suggesting that the prion protein can adopt many prion conformations, some of which could cause infection across species barriers. It was thus suggested that a similar phenomenon may explain the infection of humans with nvCJD by prions derived from BSE infected cows. However, although yeast prions have been used as a model for transmission of mammalian prions between species, there has been no suggestion of infection of mammalian species with yeast derived prions.

As described above, at present, TSEs such as nvCJD in humans are believed to be caused predominantly by exposure to infected meat products. However, certain other factors may increase or decrease the likelihood of an individual becoming infected with a TSE. Polymorphisms in the prion protein gene are known to affect incubation duration in humans and other animals. However, large differences in incubation times still occur even with the same amino acid sequence of the prion protein, suggesting that other genes are also involved. Some genotypes of sheep often develop scrapie, e.g. in the UK the genotypes: Ala136Ala, Arg154Arg, Gln171Gln and Val136Val, Arg154Arg, Gln171Gln are almost always identified in scrapie infected sheep. In contrast sheep with Ala136Ala, Arg154Arg, Arg171Arg are generally resistant to both scrapie and BSE challenge. However, the genotype does not confer scrapie on the animal but merely susceptibility to scrapie infection: the susceptible genotypes are common in Australia but nevertheless do not develop the disease, indicating that scrapie is an infectious disease, not a genetic one. Similarly, certain genes associated with susceptibility to prion disease have been identified in mice (Lloyd et al, Proc Natl Acad Sci USA 2001, 98:6279-6283). Mouse and human genomes are very similar, making it highly likely that human prion susceptibility alleles will be identified.

According to the UK CJD Surveillance Unit, the number of reported deaths of definite and probable cases of CJD in the UK is currently approximately 80 per year with 89, 84, 81, 80 and 63 deaths reported in 1998, 1999, 2000, 2001 and 2002 (up to 2 December) respectively. However, due to the long incubation time of the disease, it is feared that the incidence both in the UK and worldwide may increase considerably in the next few years. To date, however, there is no known cure for TSEs such as nvCJD. There is therefore a need for a better understanding of the pathophysiology of prion disease, as well as the development of possible treatments.

SUMMARY OF THE INVENTION

While studying the effects of *Candida* infection on mice, the present inventors have surprisingly shown that mice exposed to prolonged administration of *Candida* exhibit neurological symptoms similar to those associated with sheep scrapie. As described in the examples, subsequent analysis of the brain tissue of affected mice demonstrated the presence of prion proteins in capillary walls and intracellular spaces as well as conspicuous microcavitation in intracellular spaces especially in the frontal lobe area, suggesting that, contrary to conventional wisdom, prion related disease in mammals may be induced by exposure to *Candida* infection.

Without being limited to any one theory, the present inventors believe that *Candida* may induce or accelerate the induction of the conformational change from host proteins PrPc to the prion form (PrPsc). Alternatively, the prion proteins may be produced by *Candida* toxins. Therefore, in either case, by reducing the presence of *Candida* in a mammal, the development of prion related disease may be inhibited.

The demonstration of the link between prion disease and *Candida* infection thus makes available for the first time novel methods of treating, diagnosing and preventing transmissible spongiform encephalopathies.

Accordingly, in a first aspect of the present invention, there is provided a method of reducing the susceptibility of an individual to prion disease comprising administering an anti-*Candida* agent to said individual.

For the purposes of the present invention the term "prion disease" is interchangeable with "prion related encephalopathy" and "transmissible spongiform encephalopathy" and include any disease caused by a prion agent. Examples of such diseases include Creutzfeldt-Jakob disease (CJD), kuru, Fatal Familial Insomnia (FFI), Gerstmann Straussler Scheinker syndrome (GSS), Alpers syndrome, scrapie, bovine spongiform encephalopathy (BSE), transmissible mink encephalopathy (TME) and chronic wasting disease (CWD).

By administering the anti-*Candida* agent to a mammal, the expression of infective prion proteins in the tissues of the mammal may be reduced and the likelihood of development of prion related encephalopathies reduced accordingly. As demonstrated in the examples, the presence of *Candida* apparently facilitates the conversion of non infective PrPc proteins to infective PrPsc prions. Therefore, as well as enabling reduction of the likelihood of a patient developing a TSE, the present invention enables treatment of a patient with a pre-existing TSE to ameliorate or cure the condition by reducing or eliminating PrPsc.

Therefore, according to a second aspect of the present invention, there is provided a method of treatment of prion disease in an individual in need thereof comprising administering an anti-*Candida* agent to said individual.

Also provided is the use of anti-*Candida* agents in the preparation of a medicament for the treatment of prion disease. In yet another aspect of the invention, there is provided the use of an anti-*Candida* agent in the preparation of a medicament to reduce the susceptibility of a mammal to prion disease.

Where treatment is of an existing disease, e.g. prion disease, the suitability of treatment with an anti-*Candida* agent may be assessed by screening the patient for systemic *Candida* infection, in particular systemic candidiasis. The presence of systemic candidiasis in the patient may be indicative that the patient is more likely to respond to the treatment according to the invention.

Tests to determine the presence of candidiasis are routine in the art and may include culture of blood or tissue, examining samples of infected tissue under the microscope, identification of circulating anti-*Candida* antibody, passive hemagglutination assays (PHA), counterimmunoelectrophoresis assay (CIE), or the Cand-tec test (Fung et al, (1986) J. Clin. Microbiol. 24:542-547).

One of the most common serological tests for systemic candidiasis is the agglutination test developed by Hasenclever and Mitchell. 1961. J. Bacteriol. 82:570-573. This test detects antibodies to the mannan component of the *Candida* cell wall. Another test which may be used for detection of candidiasis is the precipitin test (Taschdjian, et al 1972. Am. J. Clin. Path. 57.:195-205; Taschdjian, et al, 1969-70 Sabouraudia. 7:110-117). The antigens commonly used for detection of *Candida* precipitin are derived from the cytoplasm of sonically or mechanically disrupted *Candida* cells.

In a third aspect, the present invention provides a method of screening an individual for susceptibility or predisposition to prion disease comprising:

a) providing a biological sample from said individual;
b) determining the presence of *Candida* in the sample; and
c) correlating the amount of *Candida* present with the likelihood of developing prion disease.

Any suitable biological sample may be used, for example, sputum, urine, stools, cerebrospinal fluid (CSF) or blood. In preferred embodiments, the biological sample is a blood or CSF sample.

The concentration of *Candida* in the biological sample may thus be used to assess the likelihood of developing prion related disease. A high concentration of *Candida* in the sample, especially a systemic sample e.g. a blood or CSF sample, may be indicative of a predisposition to prion related disease compared with individuals in which *Candida* is not present. For example, the presence of agglutination at a serum dilution of 1:160 when assessed by serological agglutination tests, may indicate a medium risk. The presence of agglutination at a serum dilution of 1:320-1:640 may indicate a high risk. The presence of agglutination at a serum dilution of 1:1280 to 1:2560 or greater dilution indicates very high susceptibility to prion disease compared with individuals in which agglutination does not occur at that dilution.

In assessing the risk to an individual of developing prion related disease, other factors in addition to the presence and titre of *Candida* may be taken into account. Such factors may include a family history of prion related disease and/or the presence or absence of a genotype conferring increased susceptibility to prion disease.

In addition to enabling the treatment and prevention of prion related disease, the present invention may be used as an aid to diagnosis of prion related disease. In a fourth aspect, the invention therefore provides a method of diagnosis of prion disease in an individual, the method comprising providing a biological sample from said individual and determining the presence of *Candida* in said sample. Optionally, the method may comprise the additional step of correlating the concentration of *Candida* detected with other symptoms which may be indicative of prion disease. This aspect of the invention may be particularly useful in assessing prion infection at an early stage.

As described above, definitive diagnosis of prion disease is generally only possible post-mortem. Early diagnosis at present relies on assessment of neurological and psychiatric symptoms with later investigations sometimes requiring brain and/or tonsil biopsies. The assessment of systemic *Candida* infection may thus prove useful in diagnosis at an early stage to assist in assessing the cause of clinical neurological symptoms. This may be advantageous in that it may enable earlier diagnosis at a stage prior to the appearance of pathological changes detectable by biopsy and, moreover, may thus reduce the need for subjecting the patient to such invasive tests such as brain biopsy. The present inventors have shown that administration of anti-mycotic medicaments can reduce or halt epileptic episodes in epileptic patients who have tested positive for *Candida*.

The presence of a high concentration of *Candida* in a biological sample, e.g. a blood or CSF sample from a patient, such as a concentration corresponding to that detected by agglutination at a serum or CSF dilution of at least 1:640, preferably at least 1:1280, in conjunction with the presence of one or more neurological or psychiatric symptoms of early stage prion disease may thus be suggestive of prion disease. The detection of *Candida* in such samples obtained from patients exhibiting neurological and/or psychiatric symptoms characteristic of prion related disease may be used in a preliminary diagnosis or final diagnosis of prion related disease depending on the number and severity of other symptoms exhibited by the patient and the severity of the *Candida* infection detected. For example, the determination that *Candida* is present systemically in a patient exhibiting one or more psychiatric symptoms such as dysphoria, withdrawal, anxiety, or insomnia and/or neurological symptoms such as poor memory, pain, sensory symptoms, and unsteadiness of gait may be used in a preliminary diagnosis which optionally may be subsequently confirmed by biopsy.

In a fifth aspect of the present invention, there is provided a kit for diagnosing prion disease or susceptibility to prion disease wherein the kit comprises means for the determination of the presence of *Candida* in a biological sample. In a preferred embodiment, the kit is a kit for use in the method of diagnosis of prion disease according to the fourth aspect of the invention.

As described above, the present invention may be used in the diagnosis and treatment of prion related disease. Treatment may be of an existing condition or may be prophylactic. In a particularly preferred aspect of the present invention, treatment may be by means of vaccination. Accordingly, in a further aspect of the invention, there is provided a vaccine for prion disease comprising *Candida* antigenic material as the immunising agent. The antigenic material may comprise any suitable antigenic material, natural or synthetic. For example, the antigenic material may be inactivated yeast blastospores and/or yeast blastospores that are in a swollen condition or an antigenic portion thereof.

In a further aspect of the invention, there is provided a method of vaccination against prion disease comprising administering a vaccine according to the invention to a mammal.

In a further aspect, there is provided the use of *Candida* antigenic material in the preparation of a vaccine for immunisation against prion disease.

A further aspect of the invention is an anti-*Candida* agent for use in the treatment of prion disease.

Furthermore, the inventor has also found that *Candida* infection may be associated with a number of further pathological conditions and that treatment with anti-*Candida* agents may diminish or cure these pathological conditions. In particular, as shown in the Examples, the inventor has surprisingly found that *Candida* infection was significant in patients with a variety of cancers. Moreover, when the patients were treated with anti-*Candida* agents, the cancers were cured.

Accordingly, in a further aspect of the present invention, there is provided a method of treatment of cancer in an individual in need thereof comprising administering an anti-*Candida* agent to said individual.

In preferred embodiments of the invention, the cancer is uterine cancer, prostate cancer or ovarian cancer.

Further provided by the invention is a method of reducing the susceptibility of an individual to cancer comprising administering an anti-*Candida* agent to said individual.

The invention further provides the use of anti-*Candida* agents in the preparation of a medicament for the treatment of cancer.

The invention further provides the use of an anti-*Candida* agent in the preparation of a medicament to reduce the susceptibility of a mammal to cancer.

Further, the present invention provides a method of diagnosis of cancer in an individual, the method comprising providing a biological sample from said individual and determining the presence of *Candida* in said sample. Optionally, the method may comprise the additional step of correlating the concentration of *Candida* detected with other symptoms which may be indicative of cancer.

Further, the present invention provides a method of screening an individual for susceptibility or predisposition to cancer comprising:
a) providing a biological sample from said individual;
b) determining the presence of *Candida* in the sample; and
c) correlating the amount of *Candida* present with the likelihood of developing cancer.

In a further aspect of the invention, there is provided a method of vaccination against cancer comprising administering a vaccine according to the invention to a mammal.

In a further aspect of the present invention, there is provided a kit for diagnosing cancer or susceptibility to cancer wherein the kit comprises means for the determination of the presence of *Candida* in a biological sample.

In a further aspect, there is provided the use of *Candida* antigenic material in the preparation of a vaccine for immunisation against cancer.

A further aspect of the invention is an anti-*Candida* agent for use in the treatment of cancer.

The inventor has also found that anti-*Candida* agents may be used in the treatment of a number of other conditions. Accordingly, the invention further provides a method of treatment of a condition in an individual in need thereof comprising administering an anti-*Candida* agent to said individual, wherein said condition is independently one of the following: inflammatory bowel disease; multiple sclerosis; ulcerative colitis; allergy; chronic dermatological disease; hair loss; chronic dandruff; thick, whitish deposits on the tongue; chronic inflammation of the eyes; dry eyes; rapid deterioration of vision; chronic fatigue; drowsiness; exaggerated craving for sweet food; insomnia; snoring; depression; melancholy; anxiety; memory problems; weight increase or loss; constipation; diarrhoea; flatulence; burning in the oesophagus and the stomach; hepatic and biliary problems; menstrual problems; inflammation of the ovaries; metritis vaginitis; frequent headaches of unknown origin which do not respond to treatment; recurrent cystitis; chronic prostatitis; muscular problems; cramps; joint problems; vertebrae lumbago; coldness of the extremities of the limbs; skin dryness; eczema; female sterility; male sterility; thyroid cyst; functional disorders of the thyroid; cardiac problems not shown by electrocardiogram; or combinations thereof.

It should be understood that the method of treatment of each of the conditions recited in the preceding paragraph each represents an independent aspect of the present invention.

"Treatment" includes any regime that can benefit a human or non-human animal. The treatment may be in respect of an existing condition or may be prophylactic (preventative treatment). Treatment may thus include curative, alleviation or prophylactic effects.

"Treatment of cancer" includes treatment of conditions caused by cancerous growth and includes the treatment of neoplastic growths or tumours. Examples of tumours that can be treated by the invention are, for instance, sarcomas, including osteogenic and soft tissue sarcomas, carcinomas, e.g., breast-, lung-, bladder-, thyroid-, prostate-, colon-, rectum-, pancreas-, stomach-, liver-, uterine-, cervical and ovarian carcinoma, lymphomas, including Hodgkin and non-Hodgkin lymphomas, neuroblastoma, melanoma, myeloma, Wilms tumor, and leukemias, including acute lymphoblastic leukaemia and acute myeloblastic leukaemia, gliomas and retinoblastomas.

Anti-*Candida* Agents

Any agent suitable for treatment of systemic *Candida* infection or systemic candidiasis may be used in the present invention. In preferred embodiments, the anti-*Candida* agent for use in aspects of the invention is a polyene antifungal agent or a vaccine.

Antifungals such as Amphotericin B, fluconazole, ketoconazole, and nystatin are the drugs most commonly used to treat candidiasis and may be used in the present invention. IV amphotericin B, alone or in combination with flucytosine, is recommended for the most severely affected. Fluconazole is as effective as amphotericin B. However, infections caused by *C. cruzii* do not respond to fluconazole and should be treated with amphotericin B; some other species of *Candida* are less sensitive to fluconazole than are *C. albicans*, particularly *C. glabrata*. For initial therapy, high doses of oral, or if necessary, IV fluconazole (600 mg/day or more) can be used pending species identification and results of in vitro susceptibility tests.

Pharmaceutical Compositions

Anti-*Candida* agents of and for use in the present invention may be administered alone but will preferably be administered as a pharmaceutical composition, which will generally comprise a suitable pharmaceutical excipient, diluent or carrier selected dependent on the intended route of administration.

Accordingly, the present invention extends to a pharmaceutical composition for the treatment of prion disease, wherein the composition comprises at least one anti-*Candida* agent.

The present invention also extends to a pharmaceutical composition for the treatment of cancer, wherein the composition comprises at least one anti-*Candida* agent.

Anti-*Candida* agents of and for use in the present invention may be administered to a patient in need of treatment via any suitable route. The precise dose will depend upon a number of factors, including the precise nature of the agent.

Some suitable routes of administration include (but are not limited to) oral, rectal, nasal, topical (including buccal and sublingual), vaginal or parenteral (including subcutaneous, intramuscular, intravenous, intradermal, intrathecal and epidural) administration.

For intravenous, injection, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

The composition may also be administered via microspheres, liposomes, other microparticulate delivery systems or sustained release formulations placed in certain tissues including blood. Suitable examples of sustained release carriers include semipermeable polymer matrices in the form of shared articles, e.g. suppositories or microcapsules. Implantable or microcapsular sustained release matrices include polylactides (U.S. Pat. No. 3,773,919; EP-A-0058481) copolymers of L-glutamic acid and gamma ethyl-L-glutamate (Sidman et al, Biopolymers 22(1): 547-556, 1985), poly(2-hydroxyethyl-methacrylate) or ethylene vinyl acetate (Langer et al, J. Biomed. Mater. Res. 15: 167-277, 1981, and Langer, Chem. Tech. 12:98-105, 1982). Liposomes containing the polypeptides are prepared by well-known methods: DE 3,218, 121A; Epstein et al, PNAS USA, 82: 3688-3692, 1985; Hwang et al, PNAS USA, 77: 4030-4034, 1980; EP-A-0052522; E-A-0036676; EP-A-0088046; EP-A-0143949; EP-A-0142541; JP-A-83-11808; U.S. Pat. Nos. 4,485,045 and 4,544,545. Ordinarily, the liposomes are of the small (about 200-800 Angstroms) unilamellar type in which the lipid content is greater than about 30 mol. % cholesterol, the selected proportion being adjusted for the optimal rate of the polypeptide leakage.

Examples of the techniques and protocols mentioned above and other techniques and protocols which may be used in accordance with the invention can be found in Remington's Pharmaceutical Sciences, 16th edition, Oslo, A. (ed), 1980.

Dose

The compositions are preferably administered to an individual in a "therapeutically effective amount", this being sufficient to show benefit to the individual. The actual amount administered, and rate and time-course of administration, will depend on the nature and severity of what is being treated. Prescription of treatment, e.g. decisions on dosage etc, is ultimately within the responsibility and at the discretion of general practitioners and other medical doctors, and typically takes account of the disorder to be treated, the age, sex, weight and condition of the individual patient, the active ingredient being administered, the site of delivery, the method of administration and other factors known to practitioners. For example, where the anti-*Candida* agent is fluconazole, 400 to 800 mg/day (po, or if necessary, IV) may be used.

Vaccines

Vaccines of and for use in the present invention may be prepared using any suitable *Candida* antigenic material. The antigenic material may be natural, recombinant or synthetic. In preferred embodiments, the antigenic material is or is derivable from inactivated yeast blastospores and/or yeast blastospores that are in a swollen condition or an antigenic portion thereof.

The techniques for preparation of vaccines which contain *Candida* antigenic material as active ingredient(s) is known to one skilled in the art. Typically, such vaccines may be prepared as injectables, either as liquid solutions or suspensions; solid forms suitable for solution in, or suspension in, liquid prior to injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof.

In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminium hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1',2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further examples of adjuvants and other agents include aluminium hydroxide, aluminium phosphate, aluminium potassium sulphate (alum), beryllium sulphate, silica, kaolin, carbon, water-in-oil emulsions, oil-in-water emulsions, muramyl dipeptide, bacterial endotoxin, lipid X, *Corynebacterium parvum* (Propionobacterium acnes), *Bordetella pertussis*, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.).

Typically, adjuvants such as Amphigen (oil-in-water), Alhydrogel (aluminium hydroxide), or a mixture of Amphigen and Alhydrogel are used. Only aluminium hydroxide is approved for human use.

The proportion of immunogen and adjuvant can be varied over a broad range so long as both are present in effective amounts. For example, aluminium hydroxide can be present in an amount of about 0.5% of the vaccine mixture ($Al_2O_3$ basis). Conveniently, the vaccines are formulated to contain a final concentration of immunogen in the range of from 0.2 to 200 mu g/ml, preferably 5 to 50 mu g/ml, most preferably 15 mu g/ml.

After formulation, the vaccine may be incorporated into a sterile container which is then sealed and stored at a low temperature, for example 4° C. or it may be freeze-dried. Lyophilisation permits long-term storage in a stabilised form.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1% to 2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the vaccine composition is lyophilised, the lyophilised material may be reconstituted prior to administration, e.g. as a suspension. Reconstitution is preferably effected in buffer.

Capsules, tablets and pills for oral administration to a patient may be provided with an enteric coating comprising, for example, Eudragit "S", Eudragit "L", cellulose acetate, cellulose acetate phthalate or hydroxypropylmethyl cellulose.

The invention will now be described with reference to the following non limiting description and the accompanying figures in which.

Figure 7:
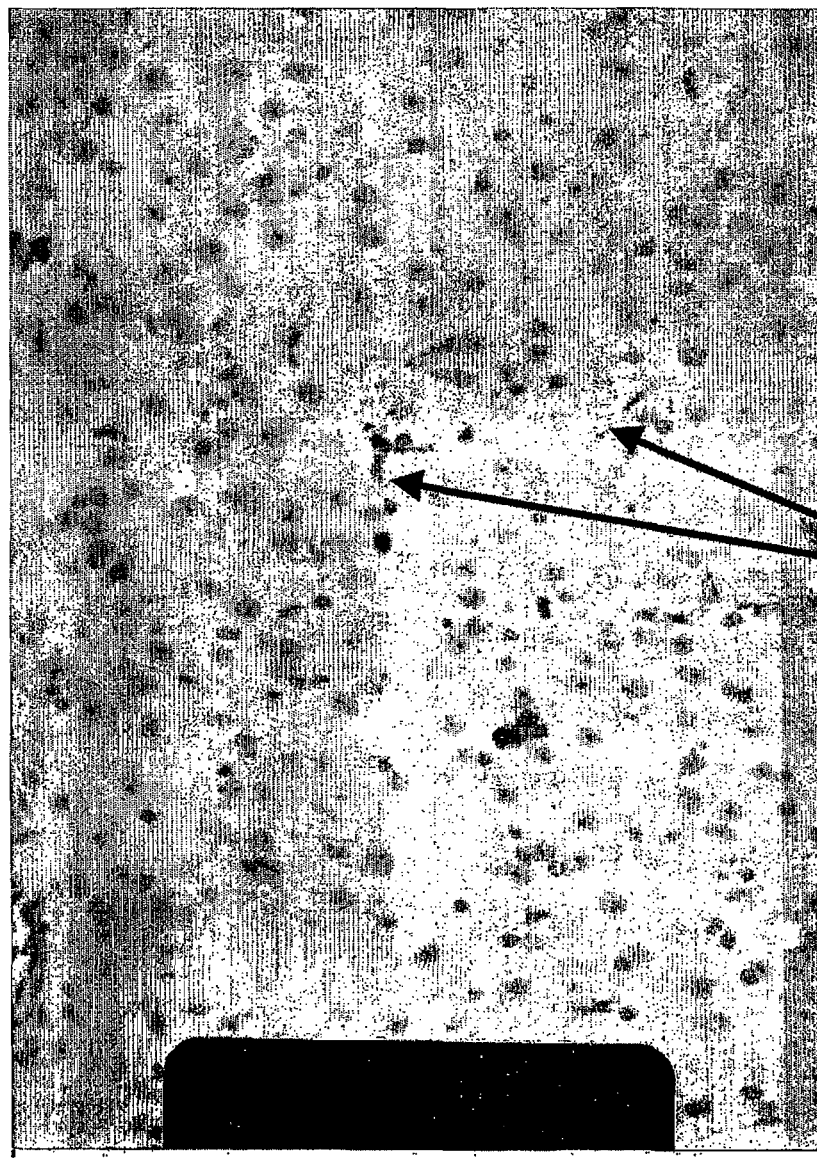

FIG. 7 shows immunhistochemistry results from a treatment mouse brain section using the 3F4 antibody to identify prion protein. Magnification 20×. Arrows indicate prions (pinkish colouration).

Figure 8:

FIG. 8 shows immunohistochemistry results from a treatment mouse brain section using the 3F4 antibody to identify prion protein. Magnification 40×.

Figure 9:
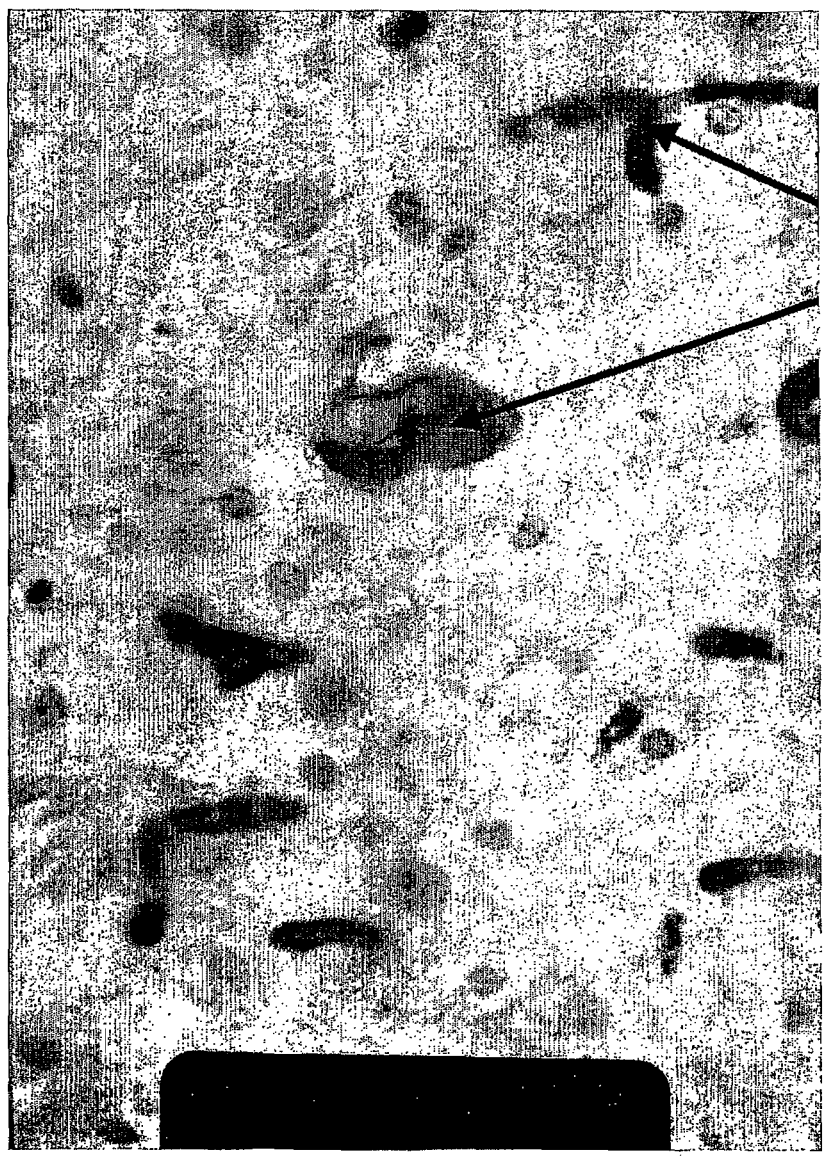

FIG. 9 shows immunohistochemistry results from a treatment mouse brain section using the 3F4 antibody to identify prion protein. Magnification 40×. Arrows indicate prions (pinkish colouration).

Figure 10:
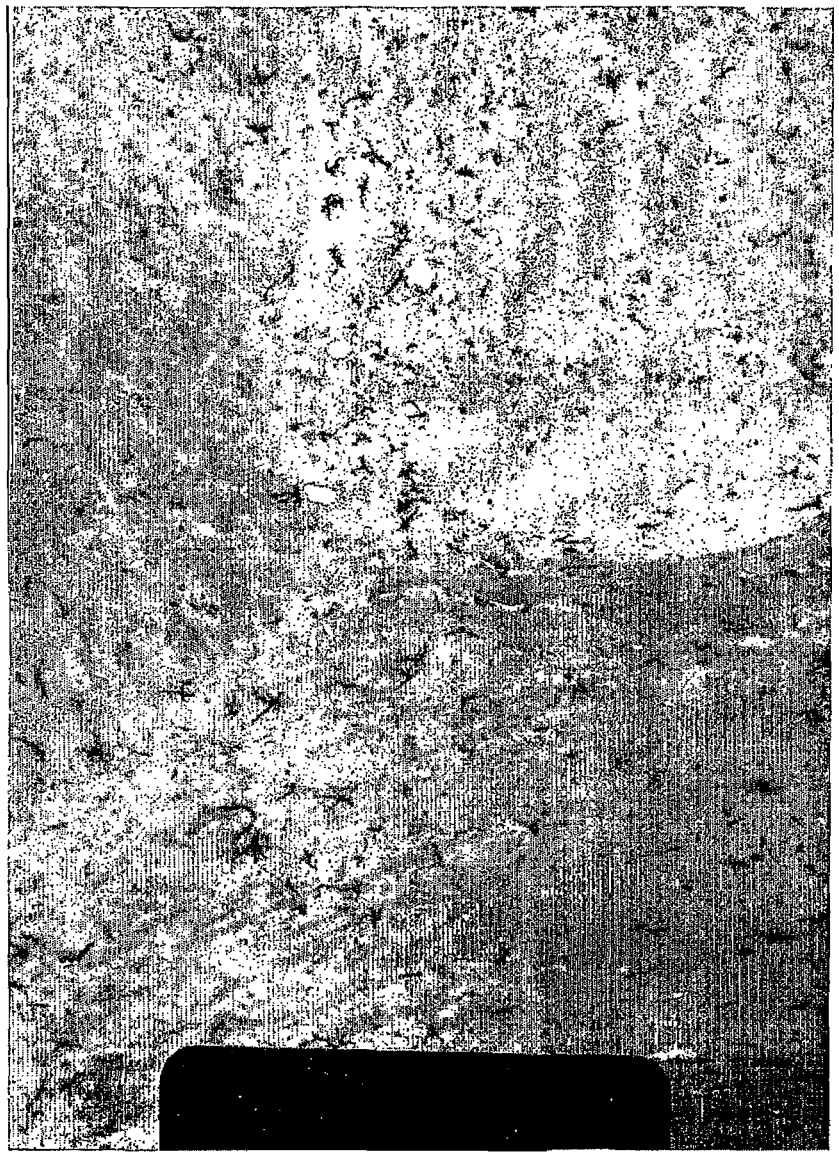

FIG. 10 shows immunohistochemistry results from a treatment mouse brain section using the 3F4 antibody to identify prion protein. Magnification 20×.

Figure 11:
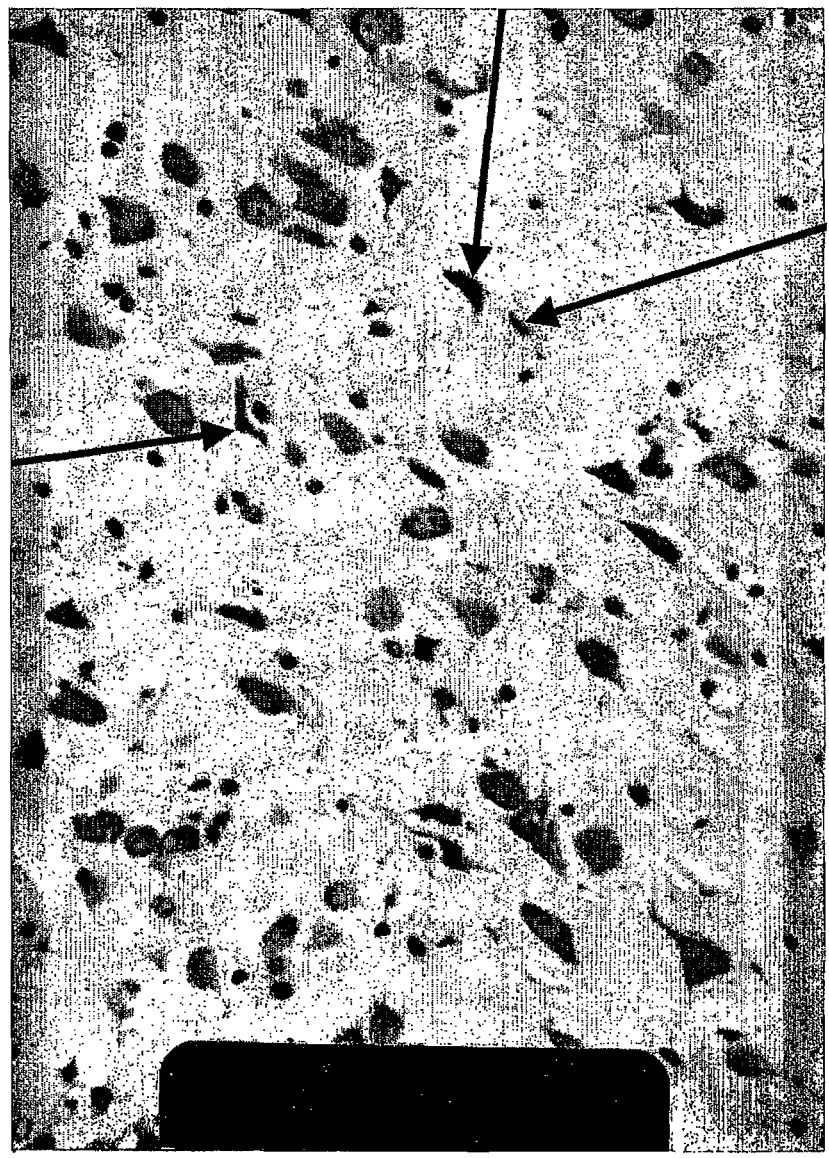

FIG. 11 shows immunohistochemistry results from a treatment mouse brain section using the method antibody to identify GFAP. Magnification 10×. Arrows indicate degenerated nerve cells.

Figure 12:
Figure 13:
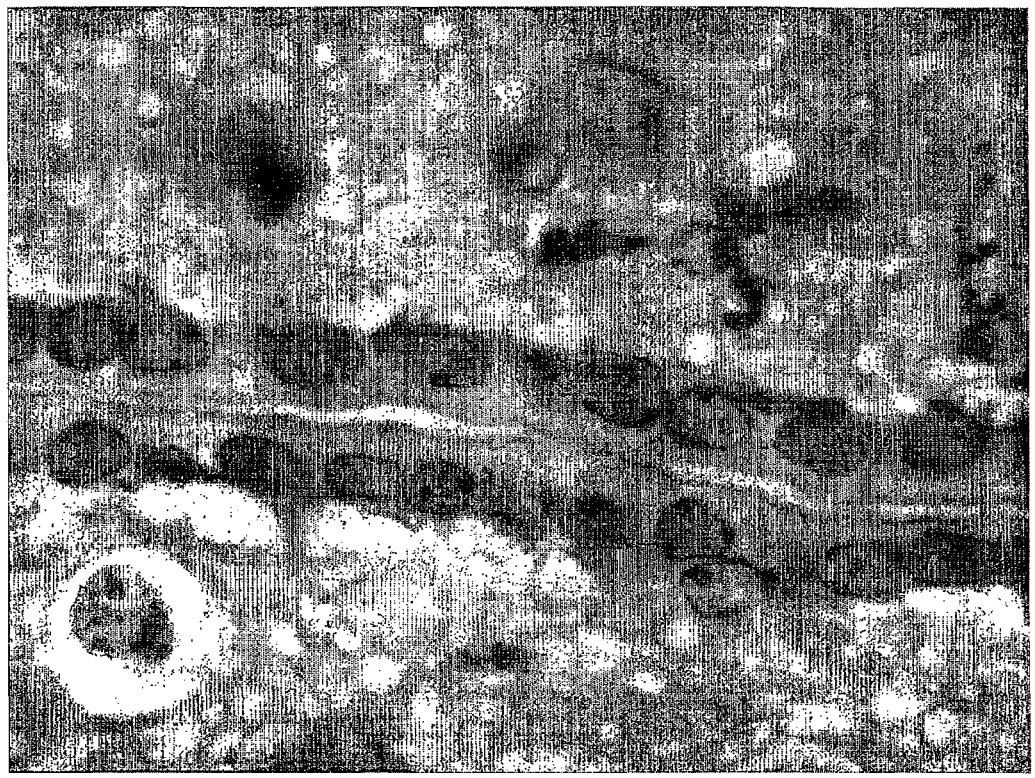
Figure 14:
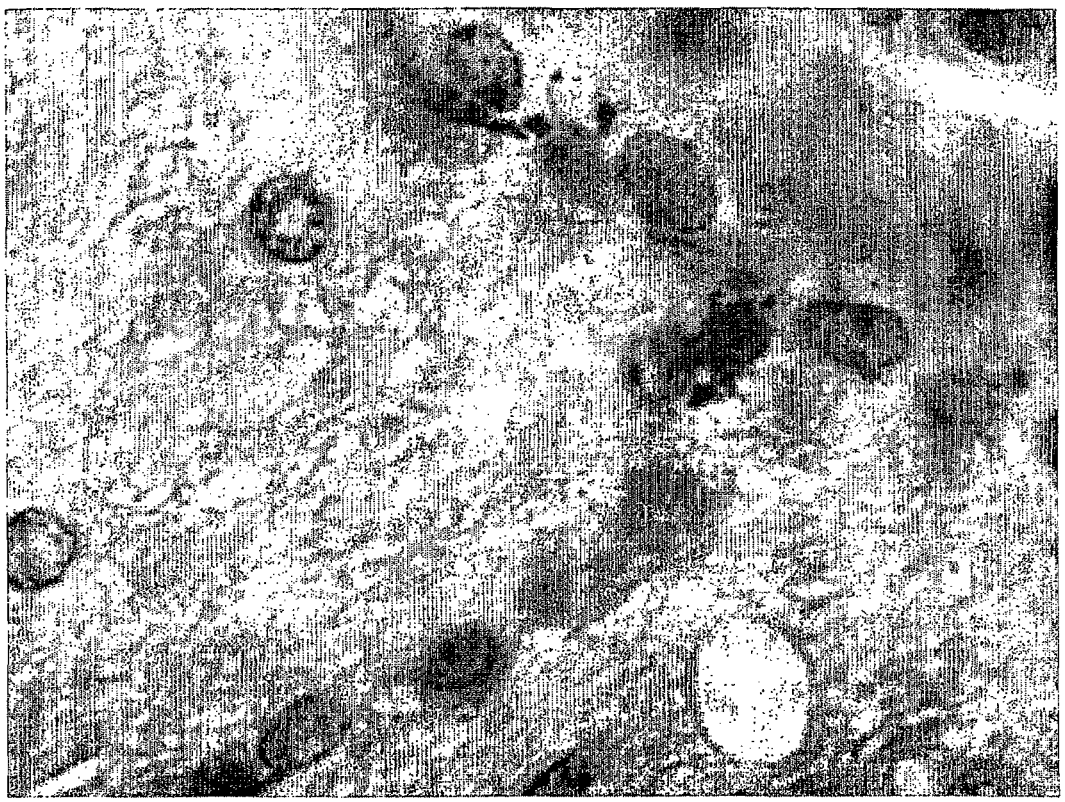
Figure 15:
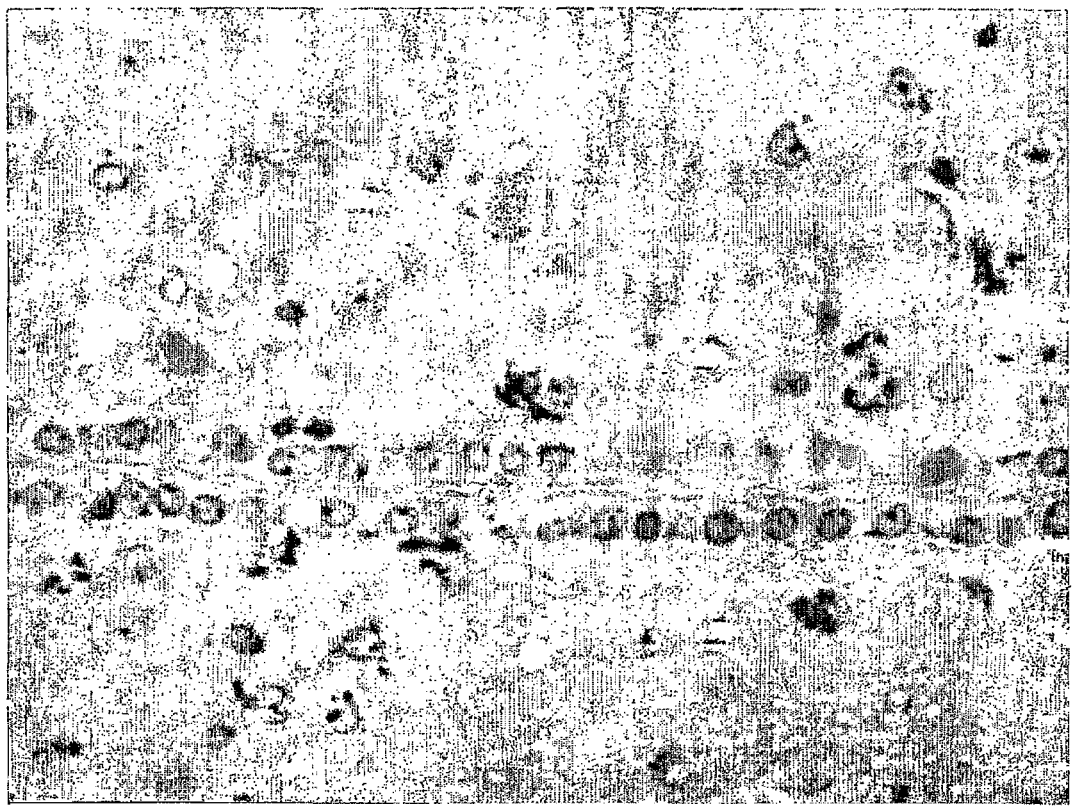
Figure 16:
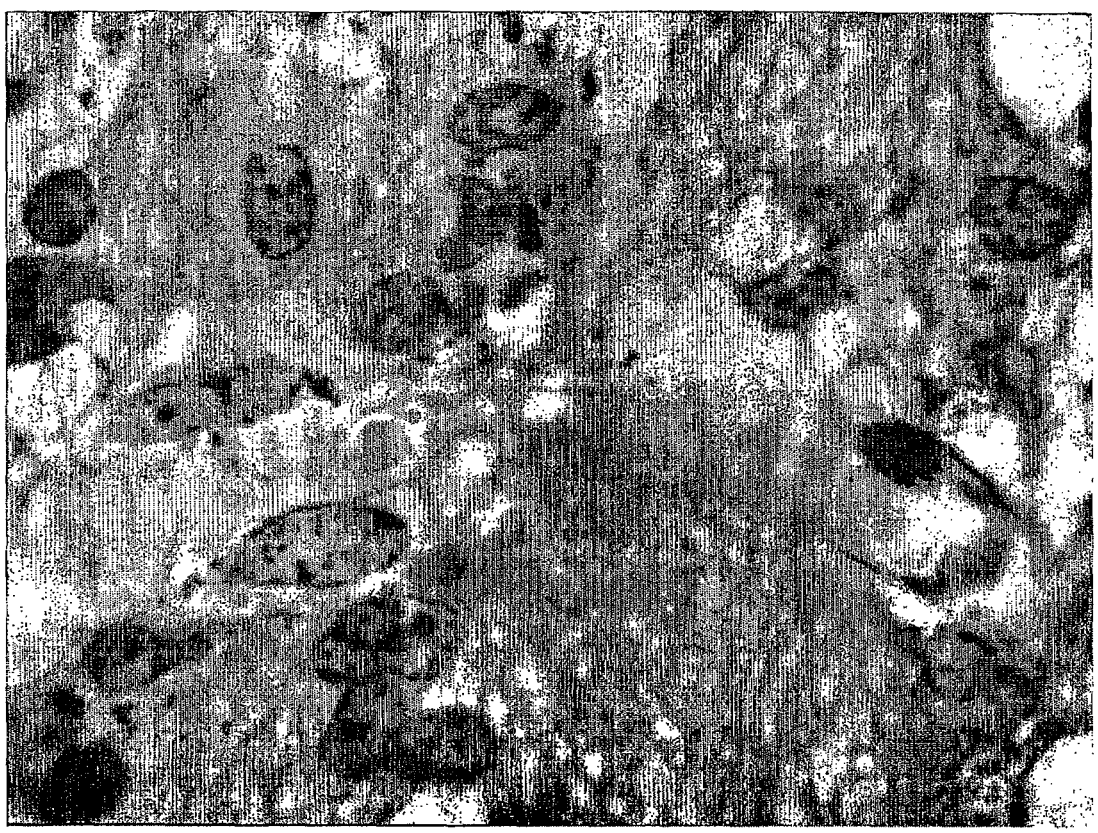
Figure 17:
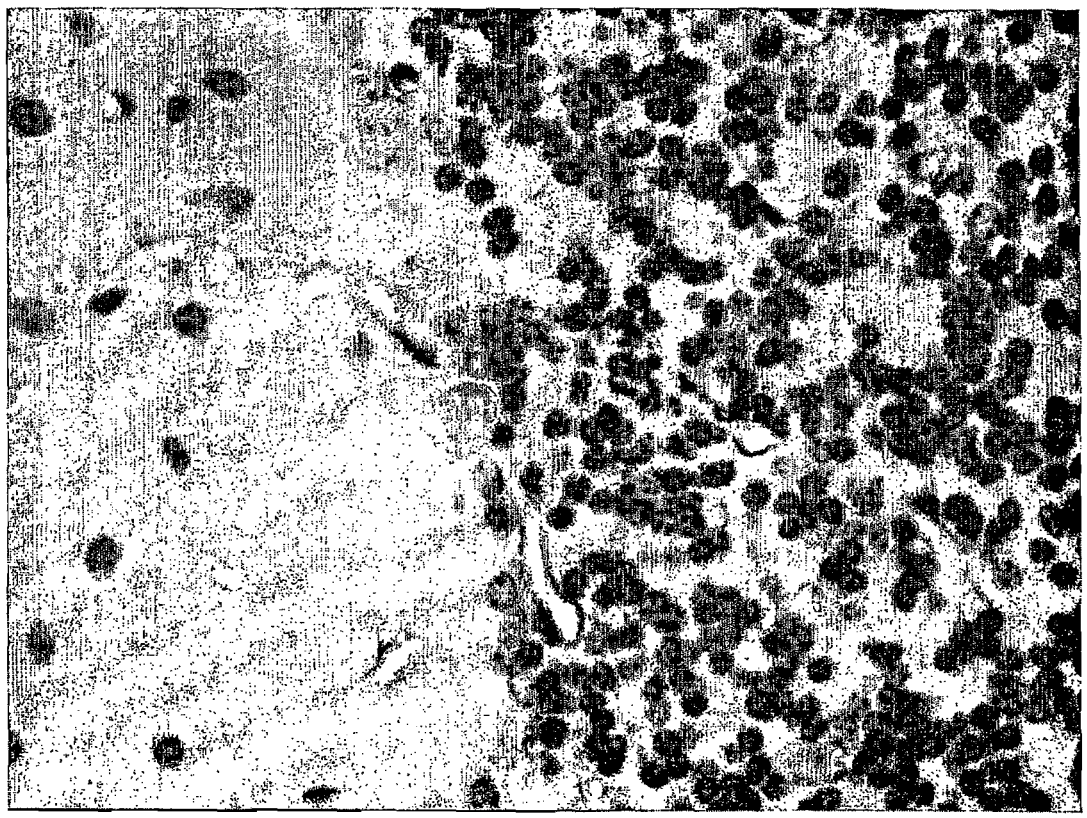
Figure 18:
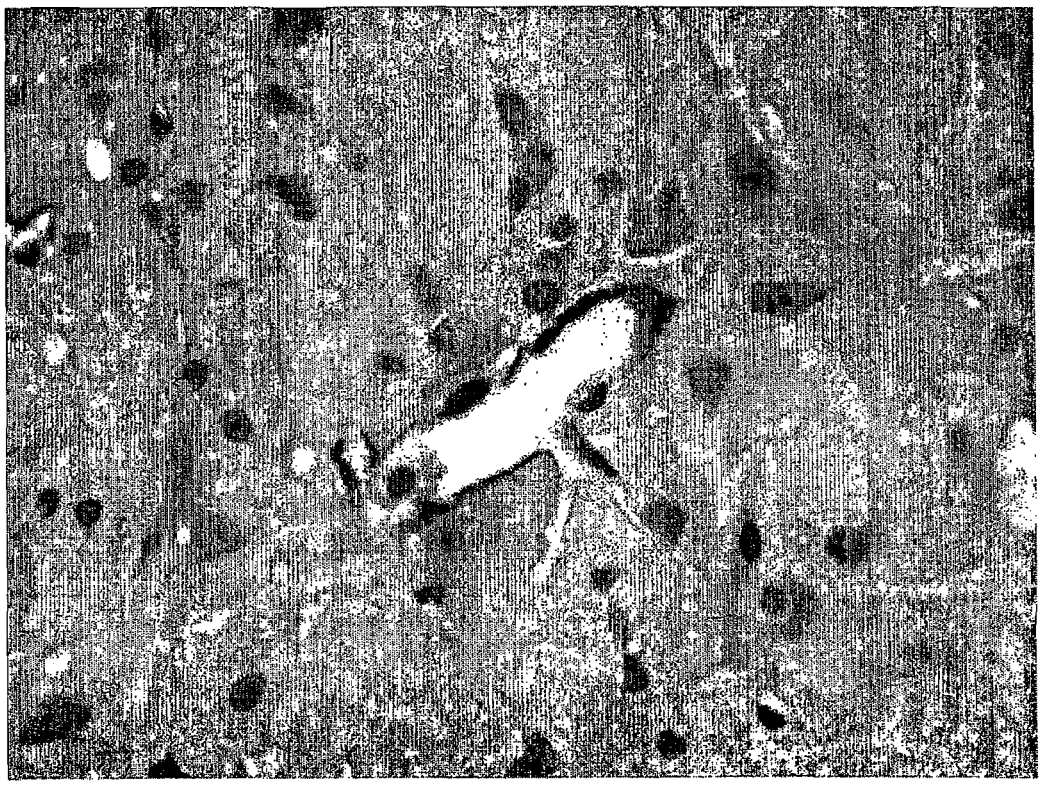
Figure 19:
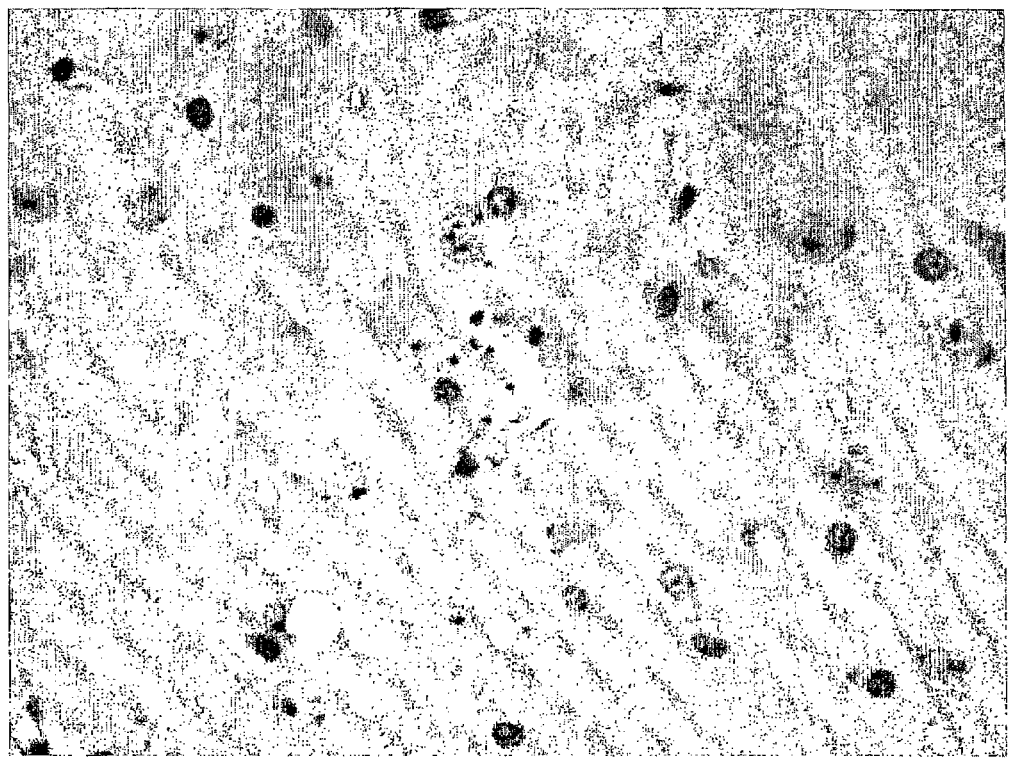

FIG. 12 shows a treatment mouse brain section stained with Cresyl, Magnification 20×.

FIGS. 13 to 19 show slides of brain sections stained with PAS. The sections correspond to those stained with Hematoxylin-Eosin and used for immunohistochemistry as shown in FIGS. 1 to 11 (Magnification ×20). The PAS colouration clearly identifies *Candida* in the brain sections.

Figure 20:
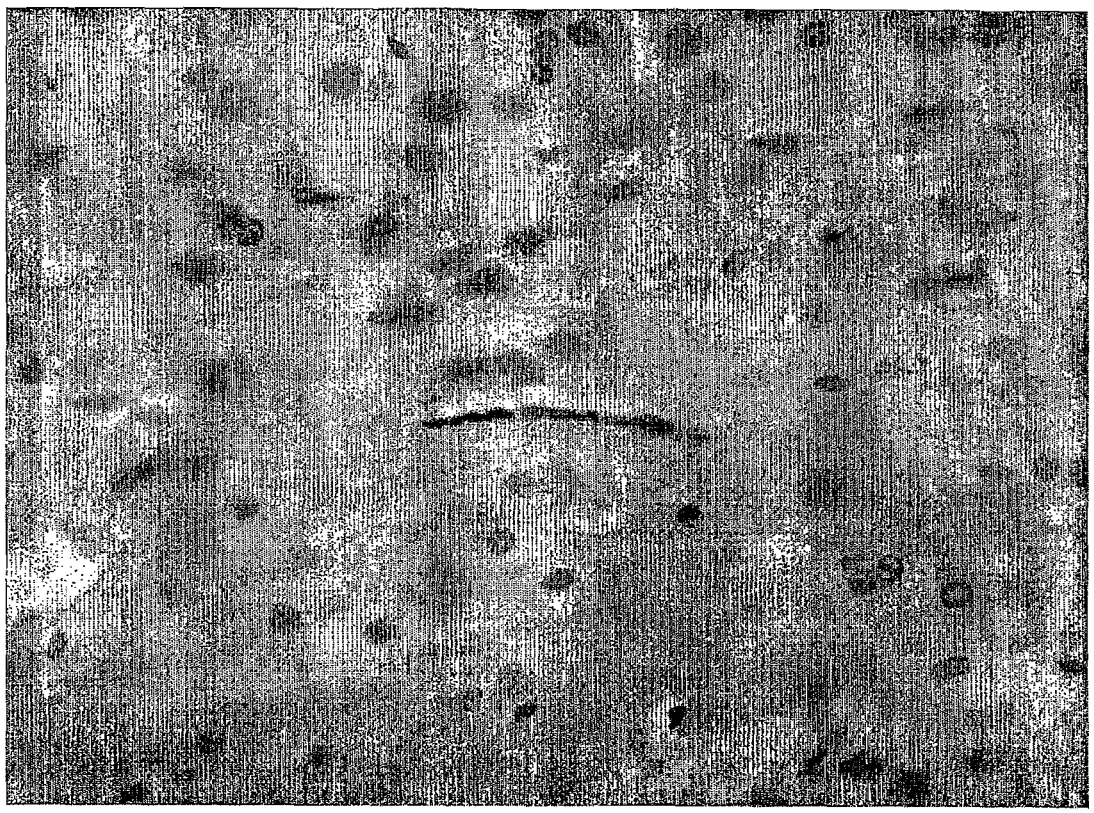

FIG. 20 shows immunohistochemistry results from a treatment mouse brain section (white matter) using the BE 12 monoclonal antibody to identify prion protein. Magnification 40×.

Figure 21:
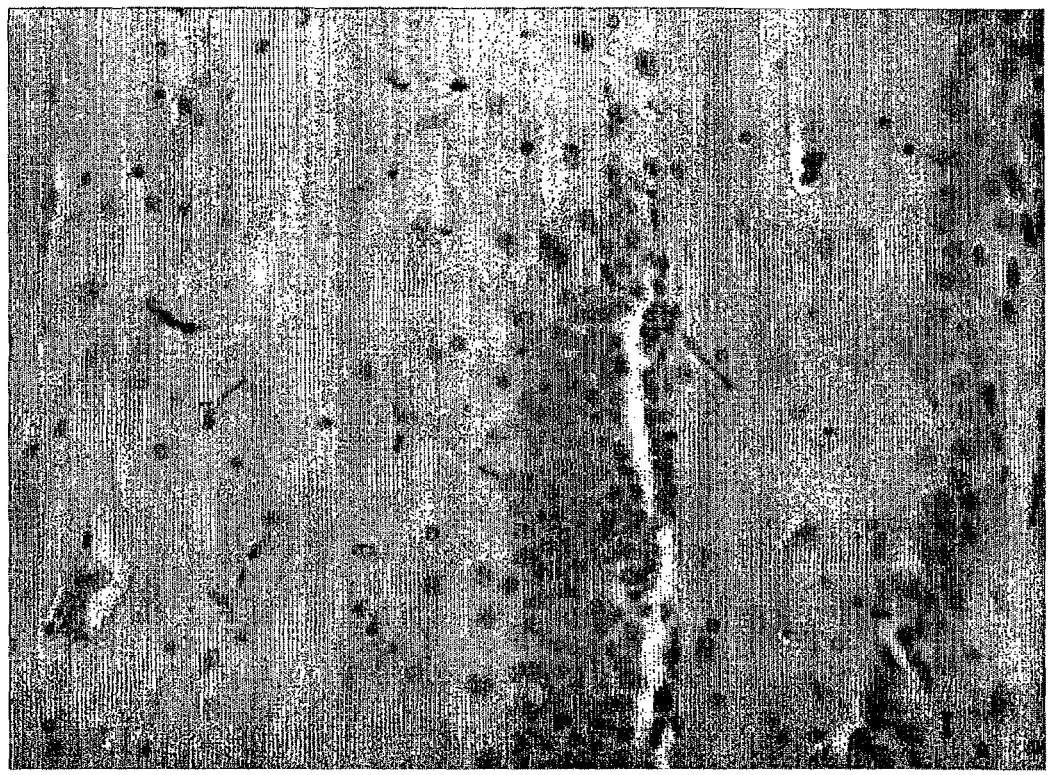

FIG. 21 shows immunohistochemistry results from a treatment mouse brain section (hippocampus) using the BE 12 monoclonal antibody to identify prion protein. Magnification 40×.

Figure 22:
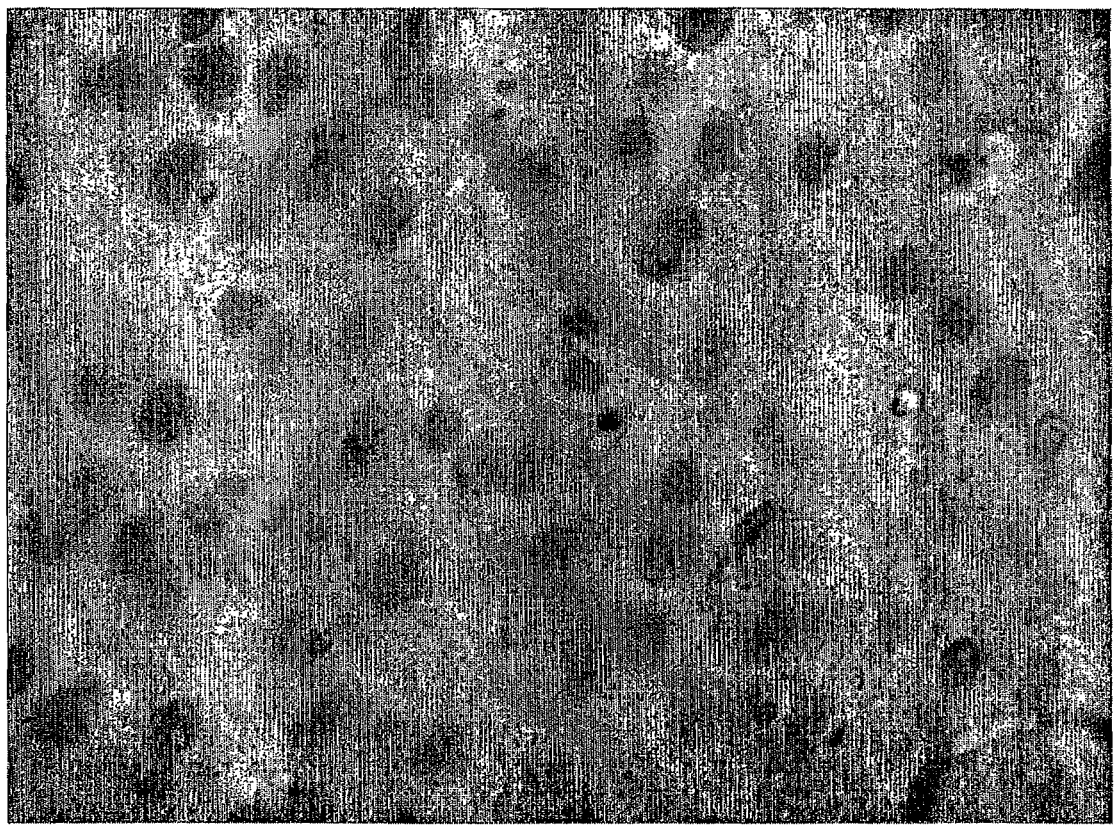

FIG. 22 shows immunohistochemistry results from a treatment mouse brain section (GLIA) using the BE 12 monoclonal antibody to identify prion protein. Magnification 40×.

Figure 23:
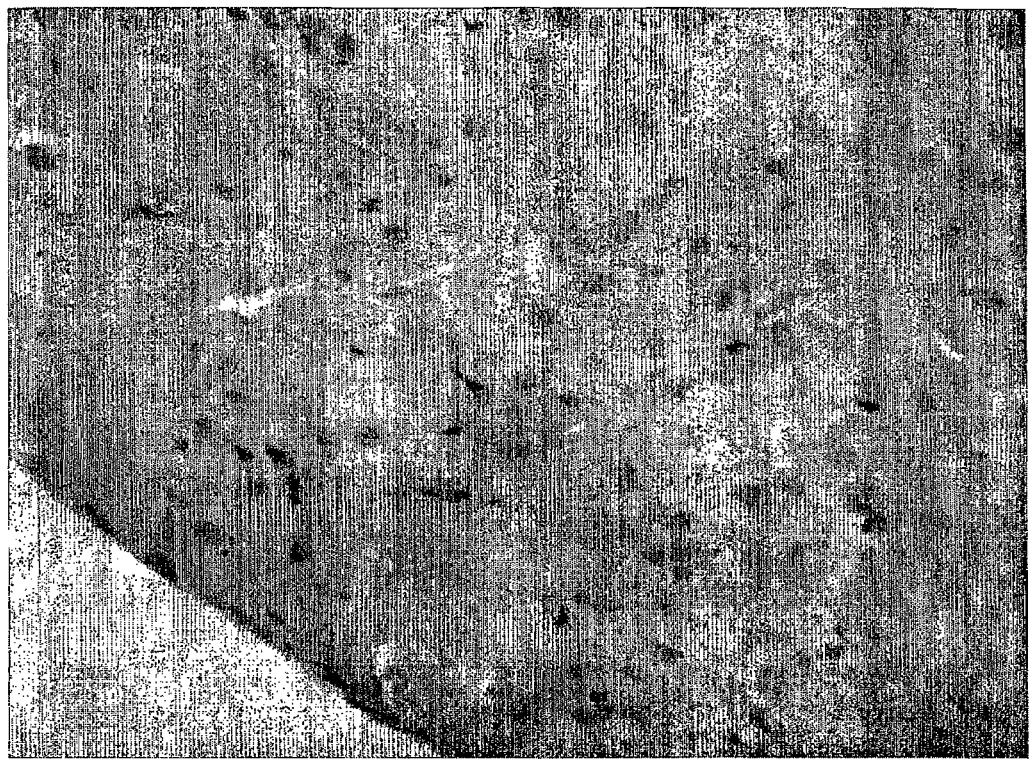

FIG. 23 shows immunohistochemistry results from a treatment mouse brain section (truncus cerebri) using the BE 12 monoclonal antibody to identify prion protein. Magnification 20×.

Figure 24:
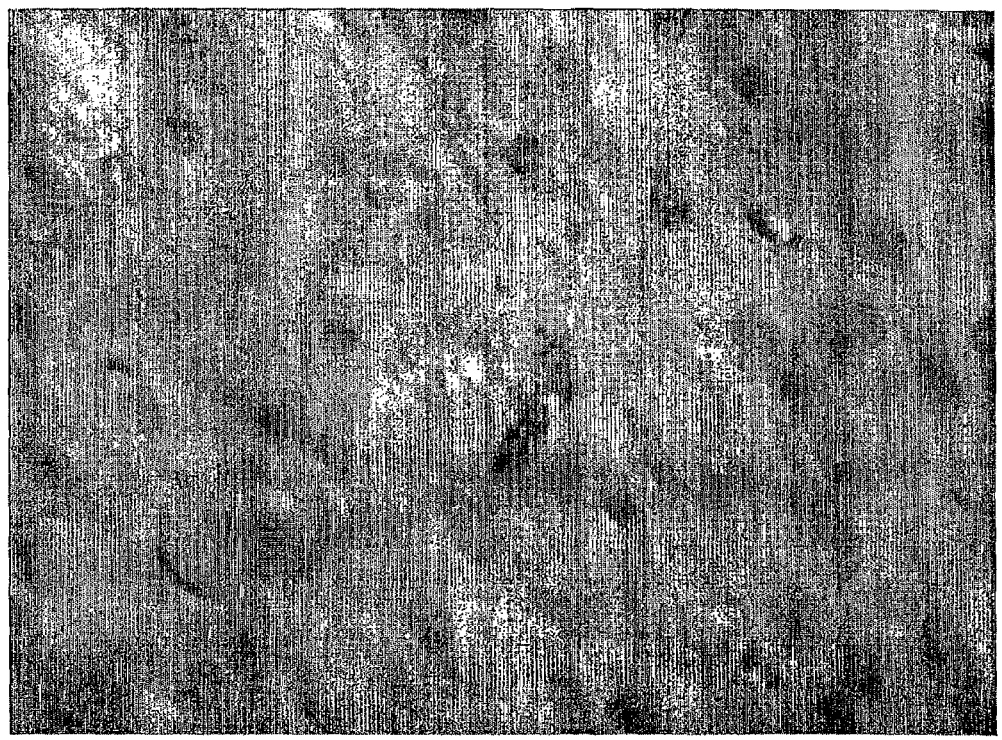

FIG. 24 shows immunohistochemistry results from a treatment mouse brain section (truncus cerebri) using the BE 12 monoclonal antibody to identify prion protein. Magnification 40×.

Figure 25:
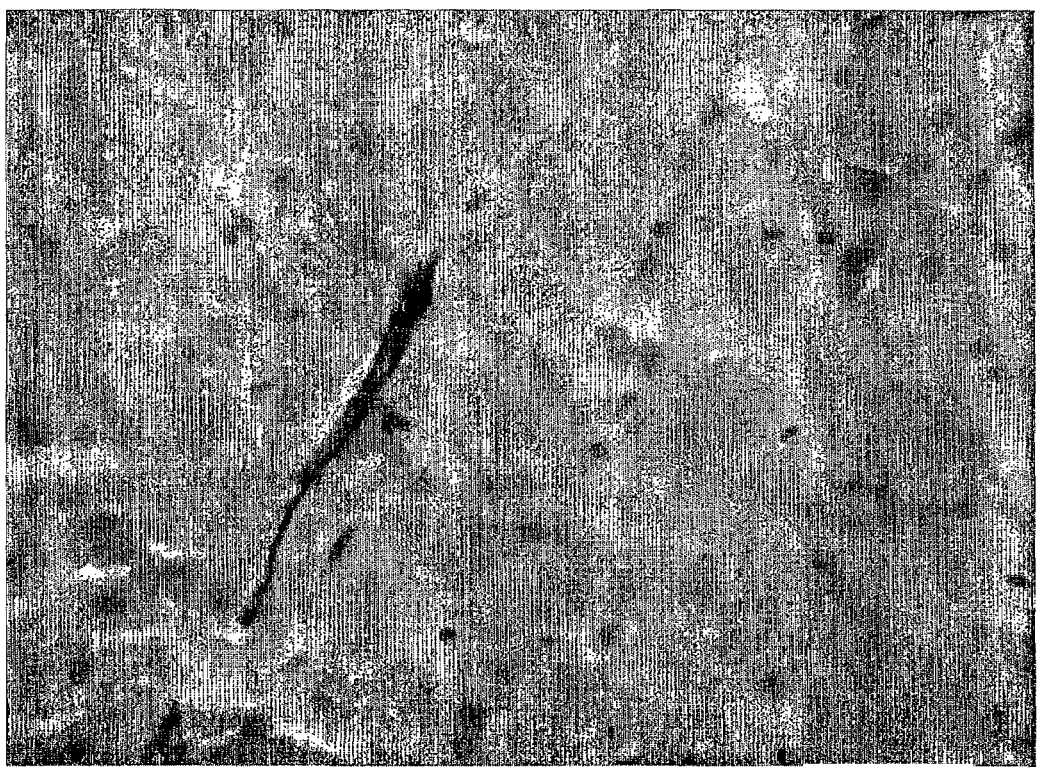

FIG. 25 shows immunohistochemistry results from a treatment mouse brain section (truncus cerebri) using the BE 12 monoclonal antibody to identify prion protein. Magnification 40×.

FIG. 26 shows a goose oesophagus section stained with Hematoxylin-Eosin.

FIG. 27 shows a goose ovary section stained with Hematoxylin-Eosin.

FIG. 28 shows a goose ovary section stained with Hematoxylin-Eosin.

FIG. 29 shows a rabbit lung section stained with Hematoxylin-Eosin.

FIG. 30 shows a rabbit oesophagus section stained with Hematoxylin-Eosin.

FIG. 31 shows a rabbit ovary section stained with Hematoxylin-Eosin.

FIG. 32 shows a rabbit ovary section stained with Hematoxylin-Eosin.

FIG. 33 shows a rabbit tongue section stained with Hematoxylin-Eosin.

FIG. 34 shows a pig brain section stained with Hematoxylin-Eosin.

FIG. 35 shows a pig kidney section stained with Hematoxylin-Eosin.

FIG. 36 shows a pig ovary section stained with Hematoxylin-Eosin.

EXAMPLES

Example 1

Administration of *Candida* to Mice Induces Prion Related Disease 5 mice (2 females and 3 males, one of which was used as control) were utilised in the study. All mice were White lab specific pathogen free mice from the National Institute of Animal Health, Department of Virology, Budapest, Hungary. Normal lab nutrition for mice was administered ad-libitum.

Hungarian and Argentinian strains of *Candida parapsillosis* and *Candida guilliermondii* were individually cultured in culture medium (Sabouraud Dextrose agar with penicillin 30 iu, Streptomycin 40 mg. per liter, sterilised in autoclave. The cultured cells were cultivated at 37° C. for a period of 72 hrs, then gathered by washing the plates with physiological solution, centrifuged and resuspended in physiological solution.

The *Candida* strains were administered to the treatment mice orally. The frequency of administration was once a week. $51 \times 10^4$ of cells per ml per Kg. of each animal's net weight was added to its drinking water. The strain of *Candida* used was alternated every two weeks starting with the Hungarian *C. parapsillosis* followed by Hungarian *C. guillermondii*, followed by Argentinian *C. parapsillosis* followed by *C. guillermondii* etc. A control mouse received no *Candida*.

The behaviour of each mouse was observed every day.

Results

After six months of administration of the *Candida* solution according to the schedule above, neurological symptoms gradually began to appear in the treatment mice as follows:

Whole body tremors

Loss of muscle control

Agitation and restlessness.

Weight loss.

Following mating, white mice delivered offspring of different colour (brown). The inventors believe that this indicates that the *Candida* may have some mutagenic effect on the DNA of the mice.

After 15 months, the last surviving mice showed serious symptoms of sheep scrapie with lesion of the skin in addition to symptoms already described in other mice used throughout the same study.

Neurohistology Results

During the first stage of the experimentation, at eight months and twenty months after the start, 2 mice were sacrificed (one male, one female) for preparation of samples for histological analysis.

All organs were perfused with Heparin in physiological solution and subsequently with Picric acid with Formalin. Histological sections were prepared and stained with Hematoxylin-eosin and Cresyl-violet stain and PAS (Periodic Acid Shiff) stain. Cresyl violet is a neurological tissue stain, which detects Nissl substance and PAS-positive material. With a PAS stain, the budding cells and pseudohyphae of *Candida* stain bright red. As can be seen from FIGS. 13 to 19, which show PAS staining of brain sections of the treated mice, *Candida* is present together with microcavitation characteristic of prion disease.

Four frontal sections were made of the mouse brain. Immunohistochemistry was performed using the 3F4 monoclonal antibody (Dako, Denmark), which detects amino acid residues 109-112 of Prion Protein (PrP) from human, hamsters, mice and felines.

Figure 1:
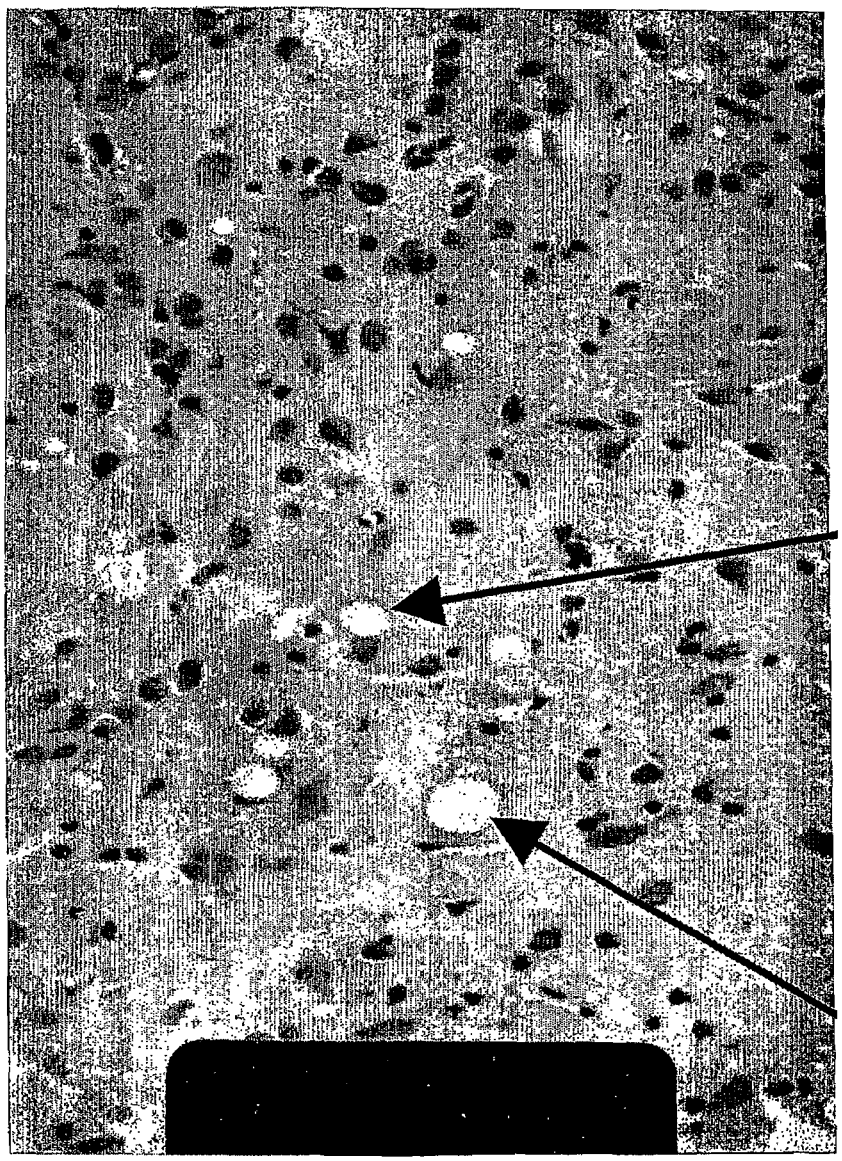
FIG. 1 shows a treatment mouse brain section stained with Hematoxylin-Eosin, magnified 20×. Arrows indicate microcavitations.
Figure 2:
FIG. 2 shows a treatment mouse brain section stained with Hematoxylin-Eosin, magnified 40×. Arrows indicate microcavitations.
Figure 3:
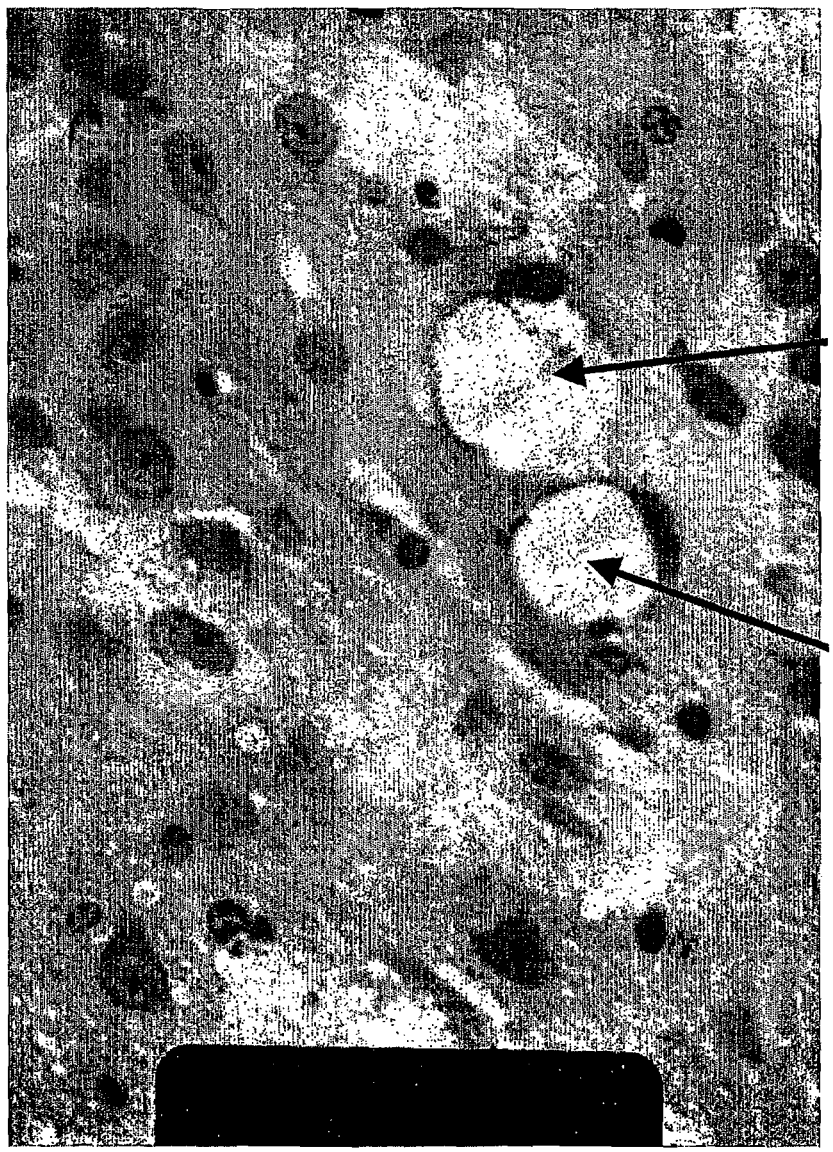
FIG. 3 shows a treatment mouse brain section stained with Hematoxylin-Eosin, magnified 40×. Arrows indicate microcavitations.

Marked presence of prion proteins in the capillary walls was observed in every section analysed using the 3F4 antibody (see FIGS. 7, 8, 9 and 10. Arrows indicate examples of prion proteins in FIGS. 7 and 9). Besides these findings, conspicuous microcavitation can be observed in the intracellular space especially in the frontal lobe area which does not seem to be an artefact (see FIGS. 1, 2, 3, 4, 5, 6. Arrows indicating microcavitations are shown in FIGS. 1, 2 and 3).

Figure 4:
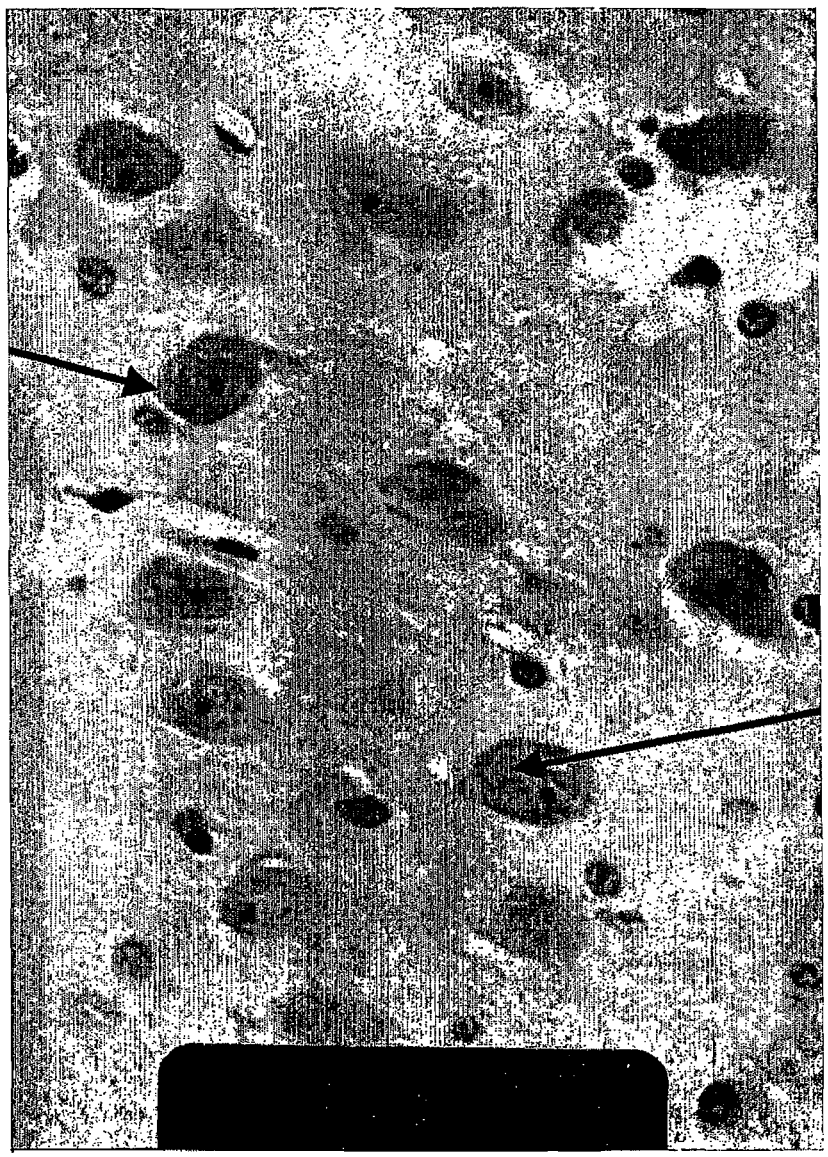
FIG. 4 shows a treatment mouse brain section stained with Hematoxylin-Eosin, magnified 40×. Arrows indicate lipofuscin (pink colouration).
Figure 5:
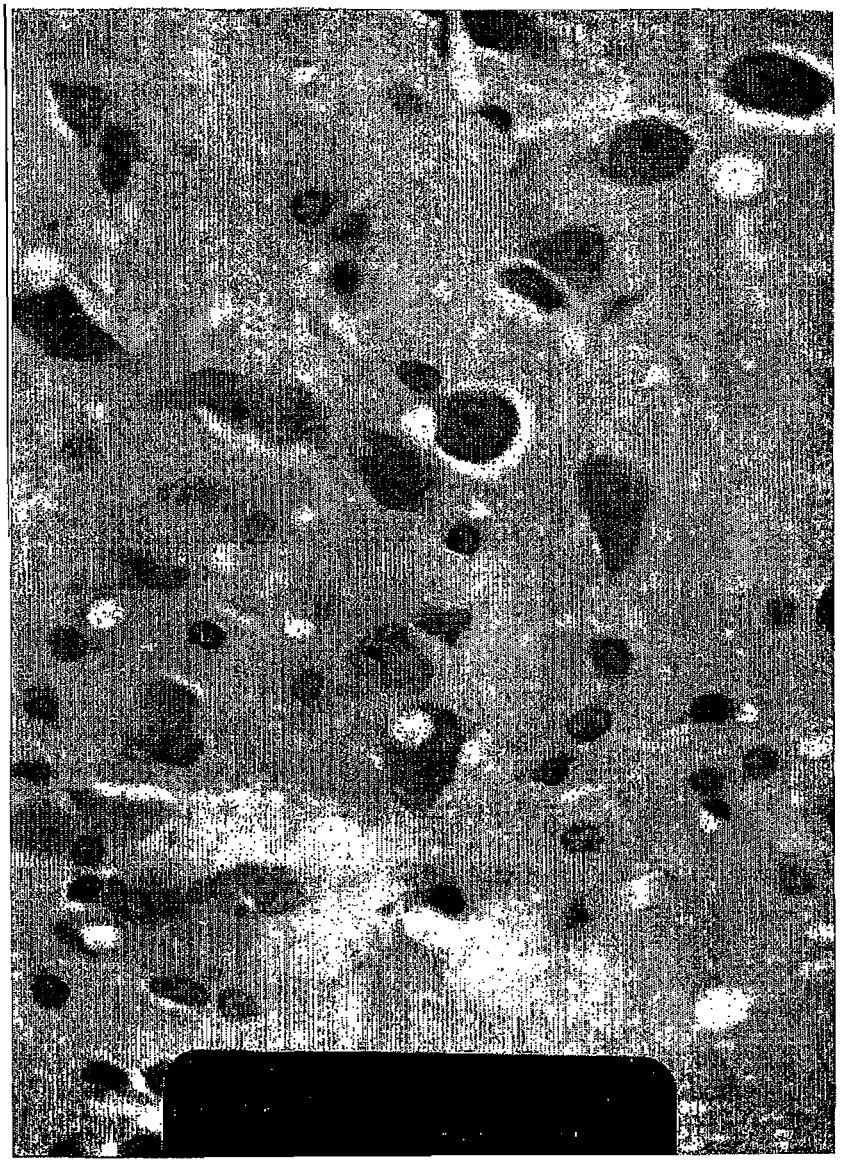
FIG. 5 shows a treatment mouse brain section stained with Hematoxylin-Eosin, magnified 40×.
Figure 6:
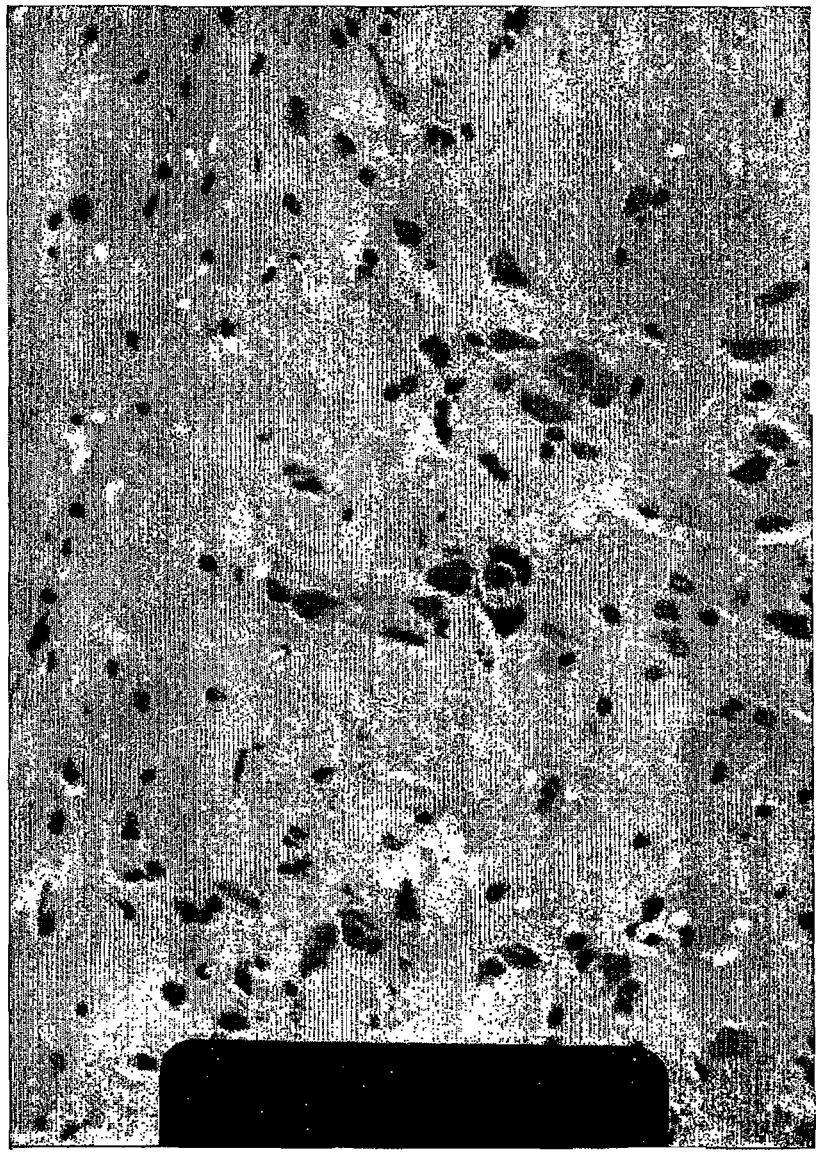
FIG. 6 shows a treatment mouse brain section stained with Hematoxylin-Eosin, magnified 20×.

Moreover, intracellular (intracytoplasmic) pink colouration was observed in the section illustrated in FIG. 4. This pink colouration (indicated by arrows) is consistent with the presence of lipofuscin, the build up of which is associated with neurodegeneration. The presence of lipofuscin in these cells therefore suggests that the prion disease induced by the *Candida* infection causes accumulation of lipofuscin which may cause or contribute to the early degeneration of the nerve cells associated with the prion infection. Degenerated nerve cells are indicated by arrows in FIG. 11.

In summary, the Examples demonstrate that mice treated with *Candida* according to the schedule described above showed signs of neurological symptoms consistent with scrapie. Post mortem brain sections demonstrated cavitation characteristic of prion related disease. The presence of prion proteins was confirmed by immunofluorescence using the prion protein specific monoclonal antibody 3F4. The neurological and morphological symptoms were absent in control animals, which were not exposed to *Candida*. The results suggest that the prion related disease has been induced by the presence of *Candida*.

To confirm the results obtained with the 3F4 antibody, the same tissue sections were re-tested using a further anti-PrP monoclonal antibody, BE 12 (Manser J. et al, TSE 2002 Edinburgh poster p 3.16), as provided by the Institute of Animal Health, Newbury, UK. Marked presence of prion proteins was demonstrated, confirming the results obtained with 3F4. The results of the immunohistochemistry using BE 12 is shown in FIGS. 20 to 25. The samples (white matter, hippocampus, GLIA, truncus cerebri, truncus cerebri and truncus cerebri respectively) were tested using BE 12 antibody in a 1:5000 dilution. Prion proteins were clearly identifiable in the samples.

Example 2

Preparation of Antigens for ELISA Tests for Diagnosis of Candidiasis

The preparation begins with a four week fermentation technique using a 10 liter fermentor of (New Brunswick). The culture medium used is: sabouraudextrose bouillon (SDB) pepton 10 gr. distilled water 100 ml; sterilised in autoclave.

After cooling down, 10% of cow serum and 30 iu of penicillin and 40 mg of streptomycin is added. The culture media is then inoculated with a *Candida* strain (for example *C. albicans, C. parpsilosis, C. tropicalis, C. guillermondii, C. glabrata, C. torulopsis, C. keyfir* etc. Fermentation conditions should be a culture temperature of 37° C. with a mixture of filtered air (4 liters per minute for a period of 10 minutes), stirred three times a day at the rate of 50 rounds per minute followed with an addition of 250 ml SDB once a day. The duration of the whole fermentation procedure lasts for four weeks.

At the end of the procedure, the medium is then centrifuged and the cell mass recovered. The cell mass is then washed in physiological solution and centrifuged three times and utilised for the production of metabolic antigens.

These antigens are then used for the fabrication of diagnostic tests, ELISA as well as for vaccination and treatment.

Antigen Production

To a 100 mg. of washed Cell Mass, 5 ml of distilled water and 50 ml mixture of Acetone-ethanol/1:1 are added and stirred. The mixture is centrifuged at 3000×g for 5 minutes.

The Supernatant is discarded and the pellet is resuspended in 10 ml of ethanol prior to further centrifugation at 3000×g for 5 minutes. The supernatant is again discarded and the pellet resuspended in 5 ml of distilled water and kept at a constant 4° C. for 10 to 12 hrs. The solution is then sonicated in a Branson cell disrupter in an ice bath for 2 hrs at 150 w with 15 min bursts. The sonicated material is then centrifuged at 4° C. at 20000 g for 60 mn. The supernatant material is used as the antigen.

The concentration of proteins is analysed by photometric absorption at 280/260 nm. The antigen is lyophilised.

Preparation of Microplates for Elisa Test 1. 10 mg of antigen is diluted in 1 ml diluent
   Dilution buffer: 0.05 M carbonate buffer, pH9.6
   Carbonate buffer: $Na_2CO_3$=1.59 g/l
     $NaHCO_3$=2.93 g/l
     Diluted in ultra high purity water.
2. Final dilution of Antigen 1:100
   With the final solution, fill up 96 wells of Nunc-Immuno plates/polystyrene with 200 µl per well (F-bottom), seal the wells with adhesive tape to prevent evaporation.

Incubate in the dark at room temperature overnight (min. 16 hrs.).

3. Wash three times (Nunc-immuno wash) in washing buffer.
   Washing buffer:
     NaCl=20.200 g/l
     Dilute in de-ionised KCl=0.20 g/l
     Water·Ph=7.2 $Na_2HPO_4$, $2H_2O$=1.15 g/l
     $KH_2PO_4$=0.20 g/l
     TRITON X-100=0.50 ml/l Preparation of Samples Before starting the test, Serum samples have to be diluted 1:200 dilution e.g. 10 µl serum+90 µl sample diluent (1:10)

10 µl hereof+190 sample diluent (1:200 in all).

First Incubation

After insertion of a sufficient number of cavities into microwell plate, 100 µl of the diluted and ready to use controls are each added to the corresponding wells. The position A1 remains empty (blank). One negative control and two standard controls are carried along.

The plate is incubated in a humid chamber at 37° C. for 30 min. The bottom of the cavities should not be in touch with materials that conduct temperature well (ie—metal or wet paper).

A1 Blank
B1 Negative control
C1 Standard control
D1 Standard control
E1, F1 Patient serum 1. 2, etc.

Warning:

The ELISA plate should not be placed in a cold moist chamber which is heated to 37° C. during the incubation. The chamber must already be adapted to 37° C. prior to the incubation Washing Decant or aspirate all microwells into a waste container with disinfectant. Ensure complete removal of the liquid from the microwells by tapping the inverted plate onto absorbant paper, then wash all wells 4 times with 300 µl of washing buffer. Be sure to remove residual washing solution by firmly tapping the inverted microwells on absorbant paper after single washing steps.

Second Incubation

Add 100 µl of 1:2000 diluted Horseradish peroxide-coupled polyvalent anti-human goat immunglobulin (DAKO) into the corresponding wells (including A1). Incubate the plate for 30 min at 37° C. in a moist chamber.

Washing

Wash 4 times according to step II.

Third Incubation

Add 100 µl of diluted Tetramethybenzidine (10 mg Tetramethybenzidine in 200 ml Citrate buffer) before the addition of 100 µl of Perhydrole (30% $H_2O$) into each well. Incubate the plate for 30 min in a moist chamber. Following the incubation, the reaction is stopped by adding 100 µl of stopping solution (1.5 N sulphuric acid solution) to each well. After carefully mixing (soft tapping on the edge of the plate), the absorbance is measured at 450 nm (optional reference wavelength 620 nm). Zero adjustment is done against the blank (position A1).

Remark

To remove moisture, wipe the bottom of the microplate before measuring.

Summary of Test Procedure

1. Bring all reagents to room temperature.
2. Dilute the serum samples.

3. Pipette 100 µl of the standard control, the negative control or the diluted samples into the microwells—30 min incubation at 37° C. in moist chamber.
4. Discard the incubate and wash 4 times with 300 µl of washing buffer.
5. Add 100 µl of diluted horseradish peroxidase coupled immunglobulin—30 min incubation at 37° C. in a moist chamber.
6. Discard the incubate and wash 4 times with 300 µl of washing buffer.
7. Add 100 µl of diluted substrate tetramethybenzidine-$H_2O_2$- 30 min incubation at 37° C. in a moist chamber.
8. After addition of 100 µl of stopping solution, spectrophotometric determination at 450 nm.

Example 3

Diagnosis of Candidiasis

Candidiasis is detected serologically using the agglutination test developed by Hasenclever and Mitchell J. Bacteriol. 82:570-573. This test detects antibodies primarily to the mannan component of *Candida* cell wall. Alternatively, candidiasis may be diagnosed using the precipitin test (Taschdjian, et al 1972. Am. J. Clin. Path. 57.:195-205; Taschdjian, et al, 1969-70 Sabouraudia. 7:110-117). The antigens commonly used to detect *Candida* Precipitin are derived from the Cytoplasm of sonically or mechanically disrupted *Candida* cells. It has been claimed that antibodies to the Cytoplasmic Antigens occur only in systemic disease.

Example 4

Preparation of Vaccine

The preparation begins with the fermentation technique using a 10 liter fermentor Type New Brunswick for 48 hours.
The culture media consists of:
Sabouraudextrose Bouillon (SDB)
Pepton 10 GR.
distilled water 100 ml
Sterilised in autoclave
After cooling down, add 10% of Cow Serum and 30 iu of penicillin and 40 mg of streptomycin.
The culture media is the inoculated with *Candida* strain. The fermentation parameter is at a culture temperature of 37° C. with addition of filtered air (4 liters per min. for 10 min.) three times a day. Stir three times a day at the rate of 50 round per min. Then addition of 250 ml of SDB twice daily.
The duration of the whole fermentation procedure lasts for 48 hrs.
At the end of the programme, centrifugation is performed, followed by recuperation of cell mass, which is then washed in physiological water and centrifuged (2000 g 30 min), three times and utilised for the production of the Immunisation Vaccine.
Preparation
The same procedure as described in Example 2, until Lyofilisation, is carried out.
Protein concentration 0.7% LOWRY 1 mg pr dose The judicious use of adjuvants is preferable to induce a strong antibody response to soluble Antigens. Most adjuvants incorporate two components. One is a substance designed to form a deposit protecting the Antigen from rapid catabolism. The two traditional methods of forming a deposit are: the use mineral oils or Alumnium hydroxide precipitates (Glenny-etal) with mineral oils, such as those used in Frund's adjuvant, the immunogen is prepared in water-in-oil emulsion.

Example 5

Administration of *Candida* to Heifers, Rabbits, Geese and Pigs Induces Serious Pathological Effects During his studies, the present inventor has shown that sterile animals infected with candidiasis, after autopsy, were all found to have tumours in their various organs (liver-kidneys-lungs-ovaries-epididymis-uterus, etc.).
Subsequently, in studies of human patients, the inventor has observed that many patients testing positive in the serological test for Candidiasis had ovary-uterus-breast and prostate tumours, which were detected by means of radiography and computer tomography.
To highlight the danger of the candidiasis pathogenesis, the inventor began an infection experiment by oral route on different types of animals.
4 heifers
48 rabbits
48 geese
16 pigs
The experiment lasted 6 months, during which the animals received a solution of a *Candida albicans*, *Candida parapsilosis* and *Candida guilliermondii* culture broth under the following conditions:
the heifers: in intravenous infusions.
the pigs: orally in unit doses.
the rabbits and geese: by stomach tube.
The solution was administered once a week.
Serological analyses of all the animals, as well as mycological analyses of the dung and stools were carried out once a month.
Results:
In the heifers, there was observed:
development of a severe constant fever.
cessation of rumen functions.
cessation of ruminating function.
All of the heifers died after one week. The heifers were sent for autopsy to the Pathology Chair of the Budapest Veterinary University and all showed the following results:
severe, acute interstitial pneumonia.
*Candida*-induced bronchopneumonia.
in the kidneys: *Candida*-induced inflammation by metastasis, with granuloma concentration.
In the pigs, there was observed:
pneumonia with granulocyte infiltration and presence of *Candida*;
in the spleen: hyperplasia and fibrosis, granulocyte infiltration and presence of *Candida*;
in the liver: granulocyte infiltration, *Candida* cells phagocyted in Kupfer cells, activation of the m.p.s (monocyte phagocyte system);
in the kidneys: interstitial inflammation, neutrophil granulocytes, infiltration into the glomerules and presence of *Candida*;
intestinal ganglia hyperplasia;
in the ileum: inflammation of the small intestine, large number of neutrophil granulocytes, and of eosinophil granulocytes, presence of *Candida* cells;
in the ovaries: vacuolisation of the ova in the primary follicles, infiltration by neutrophil granulocytes of the stroma (conjunctive tissues) of the ovaries. Presence of Candida in the atretic tertiary follicles, degeneration of the follicles in the ovaries, following toxic action by Candida;

in the brain: oedema of the brain, gliosis, lymphocytic and granulocytic infiltration, high concentration of Candida.

FIGS. 34, 35 and 36 show pig brain, kidney and ovary sections and demonstrate the presence of Candida (pink colourations) as well as agglomeration of Granuloma.

In the rabbits, there was observed:
in the spleen: hyperplasia of the malpighian body, granulocytic infiltration, presence of Candida;
in the liver: intense infiltration of the hepatic cells by lipids, infiltration by granulocytes and phagocyted Candida;
in the ovaries: atresia of the follicles, granulocyte infiltration of the stroma of the ovaries, Candida in the atretic follicles;
in the lungs: oedemas, large number of granulocytes in the alveoli, interstitial pneumonia, presence of Candida in the bronchi and the alveoli;
in the tongue: presence of Candida;
in the kidney: interstitial inflammation, presence of Candida.
in the brain: oedema.

FIGS. 29, 30, 31, 32 and 33 show rabbit lung, oesophagus, ovary and tongue sections and demonstrate the presence of Candida (pink colourations) as well as agglomeration of Granuloma.

In the geese, there was observed:
in the brain: oedema;
in the spleen: hyperplasia of the malpighian bodies, granulocytic infiltration of the pulp; presence of Candida;
in the liver: severe infiltration of the hepatic cells by lipids, proliferation of the bile duct with interstitial inflammation;
in the ovaries: presence of Candida in the atretic follicles, granulocyte infiltrations of the ovarian stroma;
in the lungs: oedema, peribronchial tissular hyperplasia, granulocytic infiltration of the pulmonary interstitium, presence of Candida in the peribronchial lumen;
in the kidneys: interstitial inflammation;
in the oesophagus: degeneration of the submucosal glands.

FIGS. 26, 27 and 28 show oesophagus, ovary and ovary sections respectively, and demonstrate the presence of Candida (pink colourations) as well as agglomeration of Granuloma.

Example 6

Administration of Anti-Candida Agents to Patients

The inventor has performed many serological tests on patients suffering from various illnesses and particularly from different types of cancer. The inventor has shown that, in many of the patients who tested positive for Candida in the serological tests, after antimycotic treatments, a full recovery was observed, with complete disappearance of the tumours in the case of the patients affected by cancer.

Some examples are given below:
Patient 1
A female patient, hospitalised, suffering from a tumour of the myoma of the uterus. While waiting for her operation (hysterectomy), she underwent a serological test which proved positive with a Candida rate of 640.
The patient was treated with Nizoral (1 tablet 2× day for two weeks, then 1 tablet a day for 30 days).

Result: Disappearance of the tumour at the end of the treatment. Shortly afterwards, normal pregnancy followed by the full-term birth of a healthy female infant.
Patient 2: Male with Prostate Cancer.
Positive for Candida serological test (640)
The patient was treated with Orungal, 100 mg capsules, 1×1 caps a day for 1 month.
Result: Complete recovery at the end of the treatment with disappearance of the tumour.
Patient 3: Female with Breast Cancer
Showed a Positive Candida serological test (320).
The patient was treated with Orungal, capsule 100 mg, 1×1 caps a day for 60 days.
Result: Complete recovery at the end of the treatment.
Patient 4: Psoriasis
Positive Candida serological test (640)
The patient was treated with Diflucan, 100 mg 1×1 capsule a day. For 1 month.
Result: Complete recovery at the end of the treatment.
Patient 5: Ulcerative Colitis.
Positive serological test (320).
The patient was treated with Orungal, 100 mg 1×1 caps a day, for 28 days.
Result: Complete recovery at the end of the treatment.
Patient 6: Female with Cancer of the Ovary with Liver Metastasis.
Positive Candida serological test (640).
The patient was treated with Diflucan, 100 mg 1 capsule a day. For 30 days
Result: Complete recovery with disappearance of the tumours.
Patient 7: Male with Prostate Cancer
Positive candida serological test (320).
The patient was treated with Nizoral (1 tablet 2× day for two weeks, then 1 tablet a day for 30 days.
Result: Complete recovery.

The inventor has also demonstrated successful treatment of the following Candida related symptoms with anti-Candida agents:
allergy; chronic dermatological disease; hair loss; chronic dandruff; thick, whitish deposits on the tongue; chronic inflammation of the eyes; dry eyes; rapid deterioration of vision; chronic fatigue; drowsiness; exaggerated craving for sweet food; insomnia; snoring; depression; melancholy; anxiety; memory problem; weight increase or loss; constipation; diarrhoea; flatulence; burning in the oesophagus and the stomach; hepatic and biliary problems; menstrual problems; inflammation of the ovaries; metritis vaginitis; frequent headaches of unknown origin which do not respond to treatment; recurrent cystitis; chronic prostatitis; muscular problems; cramps; joint problems; vertebrae lumbago; coldness of the extremities of the limbs; skin dryness; eczema; female sterility; male sterility; thyroid cyst; functional disorders of the thyroid; cardiac problems not shown by electrocardiogram.

All documents referred to in this specification are herein incorporated by reference. Various modifications and variations to the described embodiments of the inventions will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

The invention claimed is:

1. A method of treating breast, ovarian or prostate cancer in a human individual diagnosed with breast, ovarian or prostate cancer, said method comprising the steps of:
   (a) diagnosing Candidiasis in said human by detecting the presence of *Candida* infection;
   (b) subsequently to step (a), administering to the human diagnosed with Candidiasis a therapeutically effective amount of an anti-*Candida* agent selected from the group consisting of ketoconazole, fluconazole and itraconazole, wherein when said Candidiasis is due to *Candida cruzii* infection, said anti-*Candida* agent is ketoconazole or itraconazole to; and
   (c) subsequently to step (b), detecting a change in the breast, ovarian or prostate cancer in said human treated with said anti-Candida agent over the condition of the cancer before treatment.

2. The method according to claim 1, wherein said cancer is breast cancer.

3. The method according to claim 1, wherein said cancer is prostate cancer.

4. The method of claim 1, wherein said cancer is ovarian cancer.

5. The method of claim 1 comprising administration of ketoconazole.

6. The method of claim 1 comprising administration of fluconazole.

7. The method of claim 1 comprising administration of itraconazole.

* * * * *